(12) United States Patent
Lee et al.

(10) Patent No.: US 9,486,539 B2
(45) Date of Patent: Nov. 8, 2016

(54) NIPAH VIRUS ENVELOPE PSEUDOTYPED LENTIVIRUSES AND METHODS OF THEIR USE

(71) Applicant: The Regents of the University of California, Oakland, CA (US)

(72) Inventors: Benhur Lee, Los Angeles, CA (US); Karina Palomares, Los Angeles, CA (US); Olivier Pernet, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/387,371

(22) PCT Filed: Mar. 15, 2013

(86) PCT No.: PCT/US2013/032197
§ 371 (c)(1),
(2) Date: Sep. 23, 2014

(87) PCT Pub. No.: WO2013/148327
PCT Pub. Date: Oct. 3, 2013

(65) Prior Publication Data
US 2015/0050242 A1   Feb. 19, 2015

Related U.S. Application Data

(60) Provisional application No. 61/615,534, filed on Mar. 26, 2012.

(51) Int. Cl.
| | | |
|---|---|---|
| *C12P 21/06* | (2006.01) | |
| *C12N 15/63* | (2006.01) | |
| *C12N 15/00* | (2006.01) | |
| *C07H 21/02* | (2006.01) | |
| *C07H 1/00* | (2006.01) | |
| *A61K 48/00* | (2006.01) | |
| *C12N 7/00* | (2006.01) | |
| *C12N 15/86* | (2006.01) | |
| *A61K 39/12* | (2006.01) | |

(52) U.S. Cl.
CPC .............. *A61K 48/00* (2013.01); *A61K 39/12* (2013.01); *C12N 7/00* (2013.01); *C12N 15/86* (2013.01); *C12N 2740/15032* (2013.01); *C12N 2740/15041* (2013.01); *C12N 2740/15043* (2013.01); *C12N 2760/18222* (2013.01); *C12N 2760/18232* (2013.01); *C12N 2760/18234* (2013.01); *C12N 2760/18241* (2013.01); *C12N 2760/18245* (2013.01); *C12N 2810/6027* (2013.01)

(58) Field of Classification Search
USPC ........ 435/69.1, 320.1, 325; 536/23.1, 23.72; 530/395
See application file for complete search history.

(56) References Cited

U.S. PATENT DOCUMENTS

2007/0031455 A1   2/2007   Audonnet

FOREIGN PATENT DOCUMENTS

WO   WO 2007 /005244   *   1/2007

OTHER PUBLICATIONS

Leavitt et al., Concordant Modulation of Neutralization Resistance and High Infectivity of the Primary Human Immunodeficiency Virus Type 1 MN Strain and Definition of a Potential gp41 Binding Site in gp120 Journal of Virology, Jan. 2003, p. 560-570.*
Morizono et al., Redirecting Lentiviral Vectors Pseudotyped with Sindbis Virus-Derived Envelope Proteins to DC-Sign by Modification of N-Linked Glycans of Envelope Proteins.*
Palomares et al Nipah virus envelope-pseudotyped lentiviruses efficiently target ephrinB2-positive stem cell populations in vitro and bypass the liver sink when administered in vivo. J Virol. Feb. 2013;87(4):2094-108. doi: 10.1128/JVI.02032-12. Epub Nov. 28, 2012.*
Aguilar et al N-Glycans on Nipah Virus Fusion Protein Protect against Neutralization but Reduce Membrane Fusion and Viral EntryJ. Virol. May 2006 vol. 80 No. 10 4878-4889.*
Bieringet al., N-Glycans on the Nipah Virus Attachment Glycoprotein Modulate Fusion and Viral Entry as They Protect against Antibody Neutralization Journal of Virology p. 11991-12002.*
Khetawat et al., *A Functional* Henipavirus *Envelope Glycoprotein Pseudotyped Lentivirus Assay System,* 7(312) Virology Journal 1-14 (2010).
Negrete et al., *EphrinB2 is the entry receptor for Nipah virus, an emergent deadly paramyxovirus,* 436 Nature 401-405 (Jul. 21, 2005).
Palomares et al., *Nipah virus envelope-pseudotyped lentiviruses efficiently target ephrinB2-positive stem cell populations in vitro and bypass the liver sink when administered in vivo,* 87(4) Journal of Virology 4794 (abstract only) (2013).
Zhang et al, *Cell-specific targeting of lentiviral vectors mediated by fusion proteins derived from Sindbis virus, vesicular stomatitis virus, or avian sarcoma/leukosis virus,* 7(3) Retrovirology 1-15 (2010).

(Continued)

*Primary Examiner* — Maria Leavitt
(74) *Attorney, Agent, or Firm* — Karen S Canady; canady + lortz LLP

(57) ABSTRACT

The present invention relates to lentiviral particles which have been pseudotyped with Nipah virus (NiV) fusion (F) and attachment (G) glycoproteins (NiVpp-F/G). Additionally, the present invention relates to truncated NiV-F glycoproteins useful in producing such NiVpp lentiviral particles, as well as to additional variant peptides which enhance activity. Further, the present invention relates to methods of using such lentiviral particles or sequences, for example in the treatment of cancer or CNS disorders.

5 Claims, 7 Drawing Sheets

(56) References Cited

OTHER PUBLICATIONS

International Search Report mailed on Jun. 28, 2013, in corresponding PCT Application PCT/US2013/032197.
Abengozar, Maria Angeles, et al. "Blocking ephrinB2 with highly specific antibodies inhibits angiogenesis, lymphangiogenesis, and tumor growth", Blood. May 10, 2012;119(19):4565-76. doi: 10.1182/blood-2011-09-380006. Epub Mar. 23, 2012.
Alam, Syed, et al, "Coexpression of EphB4 and ephrinB2 in tumor advancement of uterine cervical cancers", Gynecologic Oncology Jul. 1, 2009;114(1):84-88. doi: 10.1016/J.YGYNO.2009.03.017.
Witting, SR, et al, "Characterization of a third generation lentiviral vector pseudotyped with Nipah virus envelope proteins for endothelial cell transduction", Gene Therapy 20, 997-1005 (Oct. 2013) | doi:10.1038/gt.2013.23.
Partial European Search Report dated Jan. 22, 2016 from corresponding EP Application 13769106.9 (EP2844746).

* cited by examiner

FIG. 1

```
NiV-F (519-544 of SEQ ID NO: 1 or 2):      EKKRNTYSRLEDRRVRPTSSGDLYYIGTDTYRYI

NiV-F T234 (519-532 of SEQ ID NO: 4):      EKKRNT....................GTDTYRYI

NiV-G (1-46 of SEQ ID NO: 10):             MGPAENKKVRFENTTSDKGKIPSKVIKSYYGTMDIKKINEGLLDSK
NiV-G Stop:                                S............................MDIKKINEGLLDSK
NiV-G Δ5 (1-41 of SEQ ID NO: 13):          MG.....KVRFENTTSDKGKIPSKVIKSYYGTMDIKKINEGLLDSK
NiV-G Δ10 (1-36 of SEQ ID NO: 15):         MG..........NTTSDKGKIPSKVIKSYYGTMDIKKINEGLLDSK
NiV-G Δ15 (1-31 of SEQ ID NO: 17):         MG...............KGKIPSKVIKSYYGTMDIKKINEGLLDSK
NiV-G Δ20 (1-26 of SEQ ID NO: 19):         MG....................SKVIKSYYGTMDIKKINEGLLDSK
NiV-G Δ25 (1-21 of SEQ ID NO: 21):         MG.........................SYYGTMDIKKINEGLLDSK
NiV-G Δ30 (1-16 of SEQ ID NO: 23):         ..............................GTMDIKKINEGLLDSK
```

NIPAH VIRUS ENVELOPE PSEUDOTYPED LENTIVIRUSES AND METHODS OF THEIR USE

CROSS-REFERENCE TO RELATED APPLICATIONS

This application is a U.S. National Stage pursuant to 35 U.S.C. §371 of International Patent Application PCT/US2013/032197, filed on Mar. 15, 2013, and published as WO 2013/148327 on Oct. 3, 2013, which claims priority to U.S. Provisional Patent Application 61/615,534, filed on Mar. 26, 2012, all of which are incorporated herein by reference in their entireties for all purposes.

STATEMENT REGARDING FEDERALLY SPONSORED RESEARCH

This invention was made with Government support under AI069317 awarded by the National Institutes of Health. The Government has certain rights in the invention.

BACKGROUND OF THE INVENTION

Lentiviruses are common vectors used in gene therapy because they can transduce non-dividing cells and offer stable integration into a target cell's genome. The host range of lentivirus vectors can be altered by pseudotyping with glycoproteins derived from enveloped viruses. Current gene therapy typically employs lentiviral vectors pseudotyped with the VSV-G envelope protein (VSV-Gpp), which has a ubiquitous host cell receptor, thereby allowing transduction of most cell types. However, VSV-G itself is known to be cytotoxic and the envelope cytotoxicity limits the amount of VSV-Gpp that can be concentrated and used for cell transduction. That is, while VSV-G envelope has great stability in the vector particle, and can be concentrated to high titers via ultracentrifugation, the toxicity of VSV-G itself limits the viral titer that can be used as too high a concentration of VSV-Gpp applied to the target cell population results in apoptotic cell death. In addition, because it has a ubiquitous host cell receptor, VSV-Gpp cannot be targeted to specific populations of cells. Additionally, when VSV-Gpp is administered intravenously to mice, the majority is trapped in the liver, sometimes termed the "liver sink" effect, which is detrimental to the gene therapy unless the desired target cells reside in the liver.

To overcome these shortcomings of VSV-Gpp, other strategies have been devised for targeted lentiviral gene therapy. One common strategy involves pseudotyping lentiviral vectors with a modified Sindbis virus envelope that has been mutated to remove its own receptor binding site and engineered to display a "ZZ" motif from proteinA—a motif that binds to the Fc region of most antibodies. Incubation of the Sindbis-ZZ pseudotyped vectors with a specific monoclonal antibody theoretically should target the lentiviral particles to the cell-type in question. (See Morizono K et al., 2005, Nat Med Vol 11(3):346-52). However, while the technique works well in vitro, in vivo the majority of the intravenously administered Sindbis-ZZ pseudotyped vector is still trapped in the liver, regardless of the antibody used. As such, improved methods of overcoming the shortcomings of VSV-Gpp are still needed.

Nipah virus (NiV) is an emerging paramyxovirus that causes acute fatal encephalitis. Two envelope glycoproteins (the fusion and attachment glycoproteins) mediate cellular entry of Nipah virus. The attachment protein, NiV-G, functions in recognition of the receptor (EphrinB2 and EphrinB3). Binding of the receptor to NiV-G triggers a series of conformational changes that eventually lead to the triggering of NiV-F, which exposes the fusion peptide of NiV-F, allowing another series of conformational changes that lead to virus-cell membrane fusion. EphrinB2 was previously identified as the primary NiV receptor (Negrete et al., 2005), as well as ephrinB3 as an alternate receptor (Negrete et al., 2006). In fact, NiV-G has an extremely high affinity for ephrinB2 and B3, with affinity binding constants (Kd) in the picomolar range (Negrete et al., 2006) (Kd=0.06 nM and 0.58 nM for cell surface expressed ephrinB2 and B3, respectively). Significantly, residues important for ephrinB2/B3 interactions with their endogenous ephB receptors are also critical for their activity as NiV receptors, indicating that the NiV attachment glycoprotein (NiV-G) can block endogenous ephrinB2-ephB4 receptor interactions.

Ephrin receptor-ligand pairs (Eph-ephrin) are membrane associated receptor tyrosine kinases (RTKs) with well-established roles in development; they regulate cell boundaries during tissue formation, and provide guidance cues during neurogenesis and angiogenesis. (See Pasquale E B. Eph-ephrin bidirectional signaling in physiology and disease. *Cell.* 2008; 133:38-52.) Cognate interactions activate both the Eph receptor (forward signaling) and ephrin ligand (reverse signaling) on opposing cells. These bi-directional signaling cascades result in cell-cell repulsion or attraction, depending on cell type or other microenvironmental cues.

EphrinB-ephB receptor-ligand interactions are a common regulator of multiple somatic stem cells, e.g., intestinal crypt stem cells and hematopoietic stem cells (Pasquale (2008) Cell 133:38-52; Poliakov et al. (2004) Dev. Cell. 7:465-480), where differentiation is a carefully choreographed molecular and cellular response to local environmental determinants. EphrinB2, in particular, has been identified as a molecular stem cell signature common to human embryonic, neural, and hematopoietic stem cells (hESC, hNSC and hHSC) (Ivanova et al. (2002) Science 298:601-604). Its cognate receptor, EphB4, has also been shown to affect mouse ESC fate. Despite much evidence from model systems that ephrinB2/ephB4 axis may be intimately involved in ESC fate (survival, self-renewal, and pluripotency), this particular axis has not been carefully studied in human ESC.

In mouse ESC, ephB4 inactivation results in bias against differentiation: ephB4-deficient mouse ESCs appear to remain in a more primitive state and are impaired in embryoid body (EB) formation in general and mesodermal differentiation in particular. (Wang et al. (2004) Blood 103:100-109)). Conversely, over expression of ephB4 in umbilical cord blood CD34+ cells results in a loss of the most primitive progenitors (LTC-ICs and CD34+/CD38− cells) likely due to differentiation into more committed precursors. (Wang et al. (2002) Blood 99:2740-2747)). EphrinB-ephB ligand-receptor interactions are promiscuous, and the lack of highly specific yet versatile reagents to interrogate this axis has hampered the understanding of ephrinB2/ephB4's role in hESC fate (pluripotency, survival and self-renewal) and HSC lineage commitment. Understanding the regulation of this signaling axis could improve the culture of hESCs and the efficiency of HSC lineage differentiation, both previously key barriers in the field.

EphB4 and ephrinB2 are both expressed in ESC and likely contribute to some aspect of stem cell fate. However, while ephrinB2 is clearly also involved in ectoderm and endoderm differentiation, ephB4 is unique amongst ephB receptors for not being expressed in the central nervous system. Thus, ephrinB2 "reverse" signaling and ephB4

"forward" signaling likely play overlapping but distinct roles in germ layer commitment and differentiation. Understanding the relative contribution of each signaling pathway may result in more optimal conditions for directing the differentiation of specific cell types.

Finally, ephrinB-ephB usually follows a gradient of ligand-receptor interactions, and expression of ephrinB2 is indeed heterogeneous within an ESC colony. Understanding the basis for the heterogeneity seen in human ES cell cultures will lead to more robust culture conditions that give rise to more homogenous population of cells suitable for regenerative medicine.

Eph-ephrin RTK expression is dysregulated in multiple cancers, and various members of this RTK family have been implicated in cancer development, progression, and subsequent metastases (See Pasquale E B. Eph receptors and ephrins in cancer: bidirectional signaling and beyond. Nat Rev Cancer. 2010; 10:165-180).

Deciphering the role of Eph signaling activities in cancer is confounded by the promiscuity of interactions between Eph-ephrin receptor-ligand pairs, and the complexity of the resultant signaling cascades. Nevertheless, the centrality of ephrinB2 in facilitating tumor angiogenesis and promoting invasion and metastasis is supported by a slew of studies that provide a sound mechanistic basis for its action (See Pasquale E B. Eph receptors and ephrins in cancer: bidirectional signaling and beyond. Nat Rev Cancer. 2010; 10:165-180). As such, soluble EphB4 inhibits tumor growth in multiple xenograft models (see Kertesz N, Krasnoperov V, Reddy R, et al. The soluble extracellular domain of EphB4 (sEphB4) antagonizes EphB4-EphrinB2 interaction, modulates angiogenesis, and inhibits tumor growth. Blood. 2006; 107:2330-2338; Kumar S R, Scehnet J S, Ley E J, et al. Preferential induction of EphB4 over EphB2 and its implication in colorectal cancer progression. Cancer Res. 2009; 69:3736-3745; Spannuth W A, Mangala L S, Stone R L, et al. Converging evidence for efficacy from parallel EphB4-targeted approaches in ovarian carcinoma. Mol Cancer Ther. 2010; 9:2377-2388), while molecular genetic evidence implicates ephrinB2 reverse signaling in the activation of VEGFR2 that leads to vessel sprouting (See Branco-Price C, Johnson R S. Tumor vessels are Eph-ing complicated. Cancer Cell. 2010; 17:533-534; Sawamiphak S, Seidel S, Essmann C L, et al. Ephrin-B2 regulates VEGFR2 function in developmental and tumor angiogenesis. Nature. 2010; 465:487-491). The latter point suggests the exciting possibility that blocking ephrinB2 signaling may synergize with anti-VEGF therapies. Furthermore, amongst all the ephrins examined, only ephrinB2 on stromal cells (fibroblast, endothelial cells, or pericytes) activates ephB3/ephB4 on invasive prostate cancer cells leading to loss of contact inhibition of locomotion (CIL), the tumor invasive phenotype responsible for cancer metastases (See Astin J W, Batson J, Kadir S, et al. Competition amongst Eph receptors regulates contact inhibition of locomotion and invasiveness in prostate cancer cells. Nat Cell Biol. 2010; 12:1194-1204; Wang B. Cancer cells exploit the eph-ephrin system to promote invasion and metastasis: tales of unwitting partners. Sci Signal. 2011; 4:pe28).

Use of Nipah virus in conjunction with a lentivirus vector has heretofore been hampered by the fact that paramyxoviral envelopes are known not to pseudotype functionally onto lentiviral particles, presumably due to some incompatibility of the cytoplasmic tail of the fusion and attachment glycoproteins with the matrix (gag) protein of HIV.

There remains a need for improved gene therapy compositions and methods that allow for enhanced delivery of the gene product to the target cells or tissues.

BRIEF SUMMARY OF THE INVENTION

The present inventors have successfully pseudotyped NiV glycoproteins onto lentiviral particles (NiVpp) by using appropriate cytoplasmic tail truncations. The inventors found that efficient functional pseudotyping requires only truncation of the F protein cytoplasmic tail, while full-length NiV-G can be used. Additional variations can also be introduced into the NiV-F or NiV-G peptide sequence to impact the properties of the resulting NiVpp lentivirus, e.g., increasing or decreasing infectivity of the NiVpp lentivirus. Codon-optimization of the NiV-F and G genes also allows for high-level expression of F and G, which enables efficient pseudotyping of NiV-F/G onto lentiviral particles (NiVpp).

NiVpp can be specifically targeted to various ephrinB2 expressing primary cells. The normal biology of ephrinB2, which undergoes rapid endocytosis upon interactions with its cognate receptor (e.g., EphB4, another membrane associated receptor-tyrosine kinase), can also be exploited. Thus, NiVpp targeted to endothelial cells may also be transcytosed across the blood-brain barrier to deliver gene-therapeutic payloads globally across the CNS. This could be useful, for example, in the treatment of Huntington's disease, which requires global correction of the gene at issue.

Additionally, the ephrinB2-ephB4 axis is dysregulated in many cancers. In some breast cancers, tumor angiogenic vessels that supply the breast cancer stroma over express ephrinB2, while in other cancers (e.g., prostate), over expression of ephrinB2 has been implicated in the loss of contact inhibition of locomotion and thus may be responsible for metastasis. As such, NiVpp could be used to target cancer cells or angiogenic vessels, for example, to treat or otherwise impact various tumors or cancers.

Finally, EphrinB2 has been implicated as a molecular signature of stemness (Ivanova, N B et al., 2002, Science, 298, 601), and the inventors have confirmed that NiVpp can specifically target subpopulations of human embryonic stem cells (SSEA4+), human neuroprogenitor stem cells (nestin+), and human hematopoietic stem cells (CD34+).

Thus, NiVpp pseudotyped lentivirus has many potential uses, including but not limited to: (1) To deliver any gene to neurons or endothelial cells, which over-express ephrinB2; (2) To deliver any gene to ephrinB2+ embryonic, neural, and hematopoietic stem cell populations; (3) To target tumors over-expressing ephrinB2; (4) To target ephrinB2+ cell populations in vivo or in vitro, e.g., for better transduction of neural stem cells for eventual transplantation; (5) To deliver therapeutic genes across the blood-brain barrier to the CNS.

Given all of this, in one embodiment, the invention is directed to a Nipah virus envelope pseudotyped lentivirus. In another embodiment, the invention is directed to Nipah virus (NiV) glycoproteins pseudotyped onto lentiviral particles (NiVpp).

In another embodiment, the invention is directed to a method for specifically targeting or delivering a gene or peptide product to ephrinB2+ cells or cell populations using the foregoing pseudotyped lentivirus. Such methods may be used, for example, to treat cancer or to combat angiogenic vessels. In certain examples, the ephrinB2+ cells comprise embryonic, neural, or hematopoietic stem cells.

In another embodiment, the invention is directed to a method for delivering or transporting a gene or peptide product across the blood-brain barrier using the foregoing pseudotyped lentivirus.

In another embodiment, the invention is directed to a method for altering brain function in a subject comprising injection of NiVpp into specific areas of said subject's brain.

In another embodiment, the invention is directed to a method for delivering any gene or peptide product to neurons or endothelial cells which overexpress ephrinB2 using the foregoing pseudotyped lentivirus.

In another embodiment, the invention is directed to a method for targeting tumors using the foregoing pseudotyped lentivirus.

BRIEF DESCRIPTION OF THE FIGURES

This application file contains at least one drawing executed in color. Copies of this application with color drawing(s) will be provided by the Office upon request and payment of the necessary fee.

FIG. 1 shows relevant portions of the NiV-F and NiV-G glycoproteins and the mutations made thereto.

DETAILED DESCRIPTION

Figure 2:
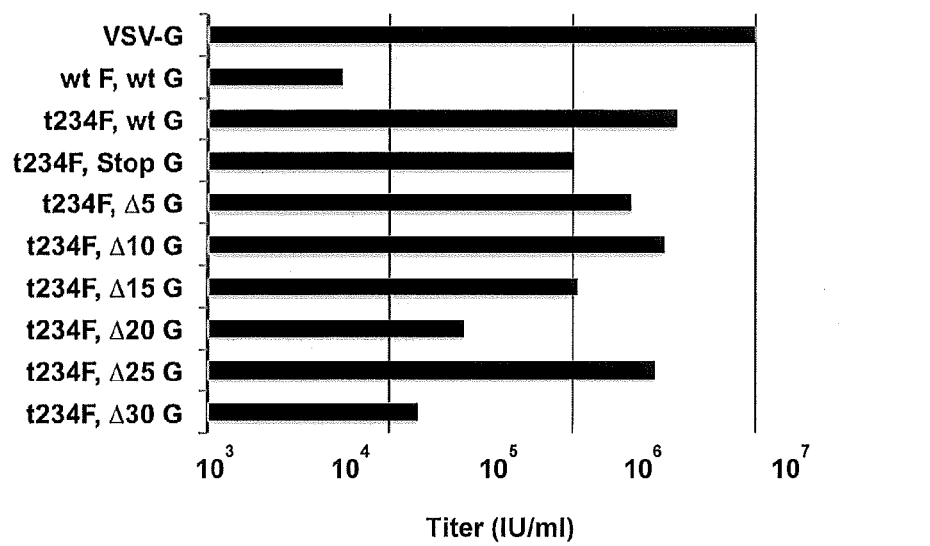
FIG. 2 shows the titer obtained from NiVpp pseudotyped lentivirus produced using various NiV-F and NiV-G truncated glycoproteins.
Figure 3:
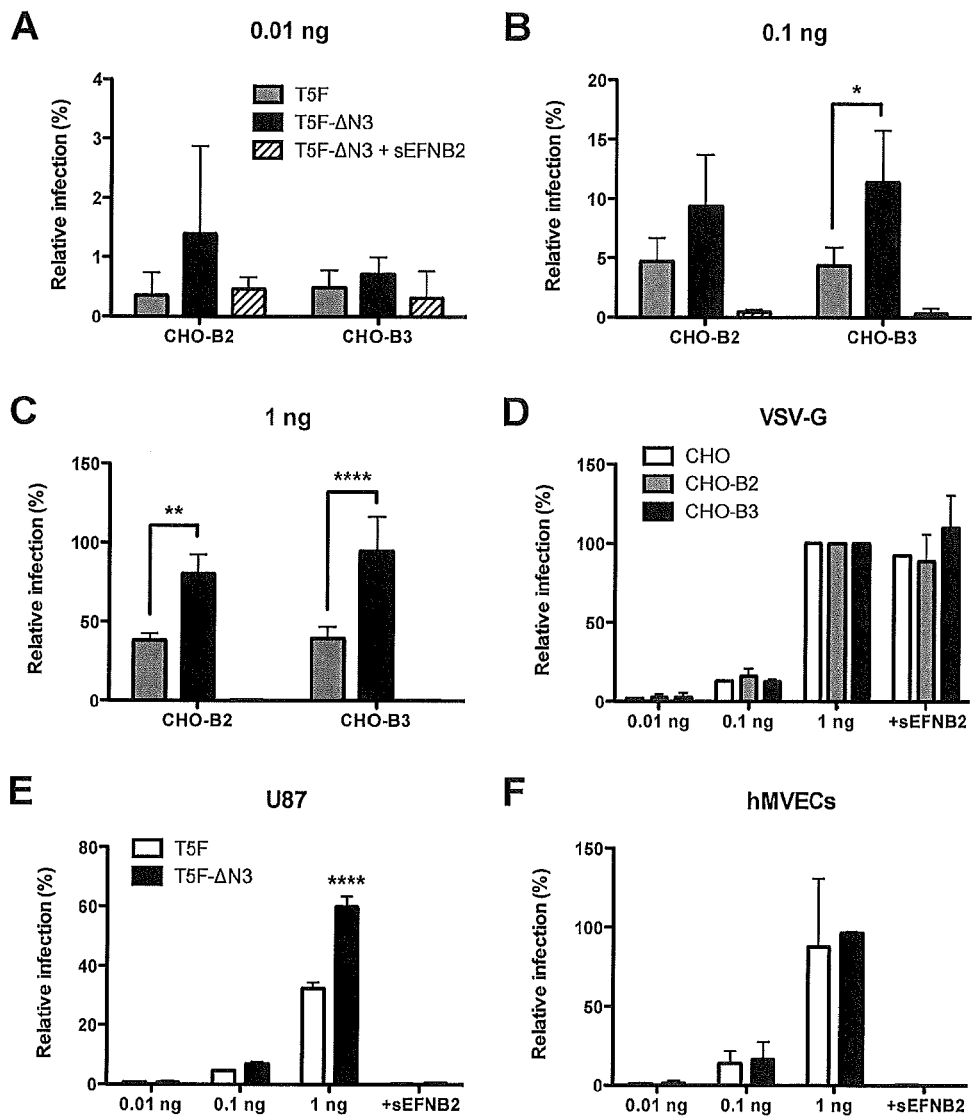
FIG. 3 shows the relative infection of various cell types by various forms of NiVpp pseudotyped lentivirus, in some cases in the presence of soluble ephrinB2. In some panels, infectivity of VSV-G is also shown.
Figure 4:
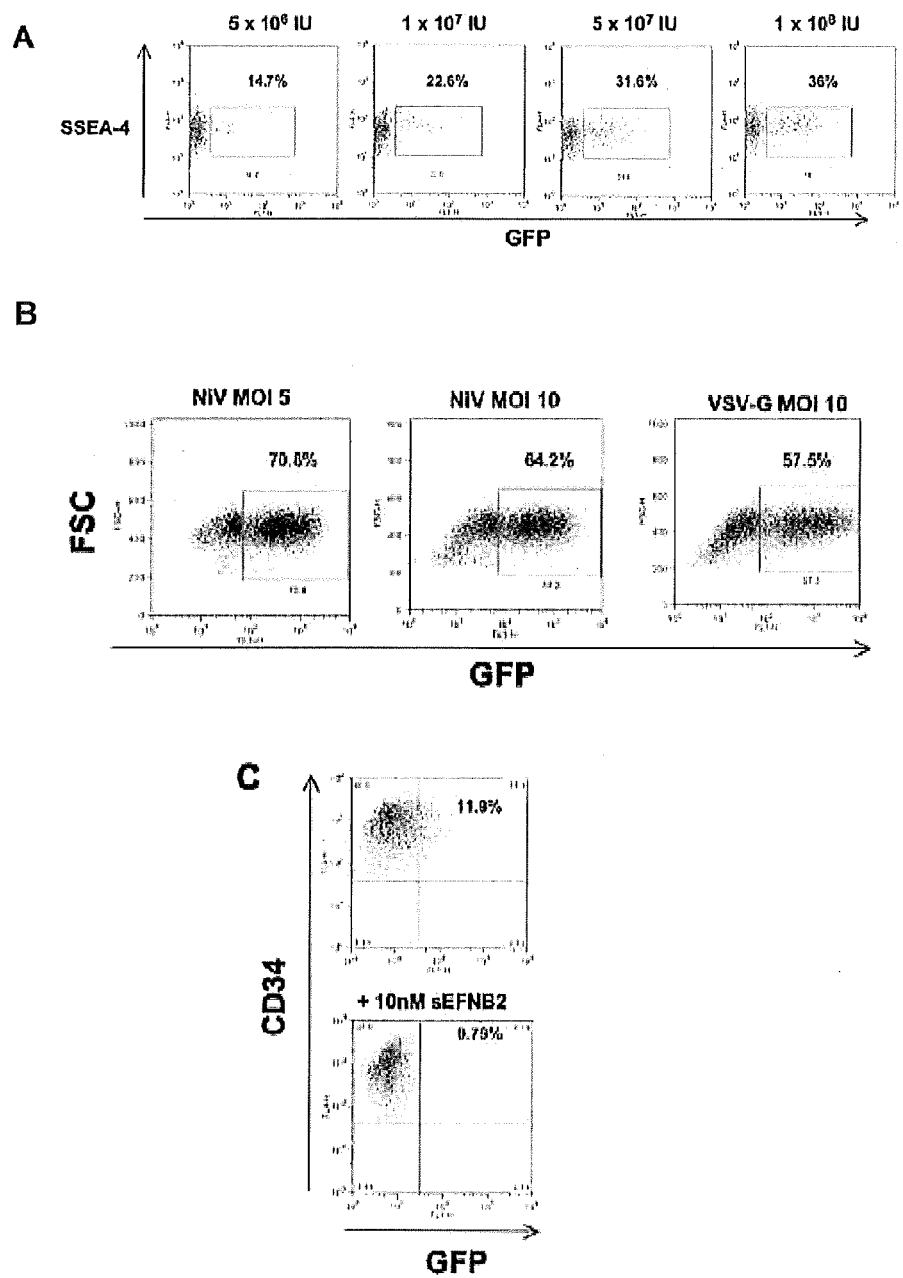
FIG. 4 shows the ability of NiVpp pseudotyped lentivirus to infect various cell types at various MOIs, in some cases in the presence of soluble ephrinB2.

Before describing the present invention in detail, it is to be understood that this invention is not limited to particular embodiments, which can, of course, vary. It is also to be understood that the terminology used herein is for the purpose of describing particular embodiments only, and is not intended to be limiting. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and polypeptide synthesis. Procedures used for genetic engineering are well known and can be found, for example, in Sambrook et al., Molecular Cloning: A Laboratory Manual, Cold Spring Harbor, N.Y.).

As used in this specification and the appended claims, terms in the singular and the singular forms "a," "an," and "the," for example, include plural referents unless the content clearly dictates otherwise. Thus, for example, reference to "polypeptide," "the polypeptide" or "a polypeptide" also includes a plurality of polypeptides. Additionally, as used herein, the term "comprises" is intended to indicate a non-exhaustive list of components or steps, thus indicating that the given composition or method includes the listed components or steps and may also include additional components or steps not specifically listed. As an example, a composition "comprising a polypeptide" may also include additional components or polypeptides. The term "comprising" is also intended to encompass embodiments "consisting essentially of" and "consisting of" the listed components or steps. Similarly, the term "consisting essentially of" is also intended to encompass embodiments "consisting of" the listed components or steps.

Numeric ranges recited within the specification are inclusive of the numbers defining the range (the end point numbers) and also are intended to include each integer or any non-integer fraction within the defined range.

In describing and claiming the present invention, the following terminology will be used in accordance with the definitions set out below.

The terms "polypeptide," "peptide," and "protein" are generally used interchangeably herein and they refer to a polymer in which the monomers are amino acids that are joined together through amide bonds. Additionally, unnatural amino acids, for example, β-alanine, phenylglycine, and homoarginine are also included. Amino acids that are not gene-encoded can also be used with the technology disclosed herein. Furthermore, amino acids that have been modified to include reactive groups, glycosylation sites, polymers, therapeutic moieties, biomolecules, and the like can also be used. All of the amino acids used herein can be either the D- or L-isomer. The L-isomer is generally preferred. As used herein, "polypeptide," "peptide," and "protein" refer to both glycosylated and unglycosylated forms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g. homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

As used herein, "NiVpp," "NiVpp lentivirus," "NiVpp pseudotyped lentivirus," NiV pseudotyped lentivirus," or the like refers to a lentivirus particle which has been pseudotyped using Nipah virus envelope glycoproteins NiV-F and NiV-G. The NiV-F glycoprotein on such NiVpp lentivirus particles is a variant form which has been modified such that it possesses a cytoplasmic tail truncation. In certain examples, the truncation will be a deletion of amino acid residues 525-544 of the NiV-F peptide, which will be referred to herein as the "T5F" or "T234F" form of the NiV-F glycoprotein (see FIG. 1). In other examples, the NiV-F glycoprotein will further include a mutation to an N-linked glycosylation site, more specifically a substitution of glutamine (Q) for asparagine (N) at amino acid position 99 of the NiV-F peptide, which will be referred to herein as the "DeltaN3" or "ΔN3" form of the NiV-F glycoprotein.

The NiV-G glycoprotein can be either a wild-type form or a modified or variant form of the protein, such as a truncated NiV-G. Deletions of 5, 10, 15, 20, 25, and 30 amino acids at or near the N-terminus of the NiV-G peptide were constructed, which are referred to herein as "Δ5G," "Δ10G," "Δ15G," "Δ20G," "Δ25G," and "Δ30G," respectively. A partial amino acid sequence of the NiV-F and NiV-G peptides showing each one of these variations is shown in FIG. 1.

The present inventors engineered the Nipah virus envelope glycoproteins to be efficiently pseudotyped onto lentiviruses, and such NiV pseudotyped lentiviruses can efficiently target ephrinB2 expressing cells in vitro and in vivo. In certain examples, the NiVpp can be used to target a subpopulation of ephrinB2+/SSEA-4+ human embryonic stem cells (hESC). In other examples, NiVpp can be used to deliver agents that antagonize EphB-ephrinB2 mediated signaling specifically to ephrinB2-expressing target cells.

Further, NiVpp is the first demonstration of any lentiviral vector administered intravenously that can bypass the liver sink, which allows for targeting of specific ephrinB2+ populations in vivo. In addition, the natural tropism of NiVpp can be altered by mutating the natural receptor binding site to make it more ephrinB2 or B3 specific, depending on the clinical context of its use. NiVpp opens up the possibility for therapeutic targeting of ephrinB2-overexpressing cells common in various solid cancers or their tumor angiogenic vessels (see E. Pasquale, 2011).

EphrinB2 and its endogenous receptor, EphB4, are both receptor tyrosine kinases that undergo bi-directional signaling as well as bidirectional endocytosis upon interaction with each other. NiVpp can take advantage of this biological property for transcytosis across the blood brain barrier. This is a critical barrier in CNS targeted gene therapy (by systemic administration). NiVpp can transcytose across functional microvascular endothelial cell layers to infect target cells at the bottom of the transwell chamber. Further, considering that NiVpp can transduce Nestin+ neural stem cells even more efficiently than VSV-Gpp, direct stereotatic injection of NiVpp into specific CNS areas where neurogenesis (proliferation of neurons from stem cell progenitors) is known to occur in the adult brain, such as the hippocampus and the subventricular zone, is possible.

The efficiency of NiVpp transduction can be improved by engineering hyperfusogenic mutations in one or both of NiV-F and NiV-G. Several such mutations have been previously described (see, e.g., Lee at al, 2011, Trends in Microbiology). This could be useful, for example, for maintaining the specificity and picomolar affinity of NiV-G for ephrinB2 and/or B3 while independently enhancing the entry efficiency of NiVpp. Additionally, mutations in NiV-G that completely abrogate ephrinB2 and B3 binding, but that do not impact the association of this NiV-G with NiV-F, have been identified. This could allow for specific targeting of other desired cell types that are not ephrinB2+ through the addition of a single chain variable fragment (scFV) directed against a different cell surface molecule The inventors have generated several mutants of the NiV fusion protein (NiV-F), and have also generated stepwise truncations in the cytoplasmic tail of the attachment protein (NiV-G), and screened each in combination with the NiV-F variant(s) for the ability to pseudotype lentivirus. Infectivity has been examined using a variety of cell types, including 293T and CHO-B2 cells, both of which express the NiV primary receptor, ephrinB2. While many of the G-truncations were expressed and could be pseudotyped onto lentiviruses, the highest increase in viral transduction titers (~100-fold) was obtained with the NiV-F variant and wild-type NiV-G, indicating that only truncations in the cytoplasmic tail of NiV-F are critical for efficient pseudotyping. Infection was blocked using soluble ephrinB2, confirming specificity of NiV pseudotyped lentivirus for ephrinB2+ cells. Moreover, NiV pseudotyped lentiviruses can suitably transduce primary human neurons and microvascular endothelial cells. Thus, lentivirus pseudotyped with NiV envelope may be used for targeted gene therapy in situations where ephrinB2/B3 is upregulated in the diseased tissue, thereby overcoming limitations of current gene therapy.

The NiVpp pseudotyped lentivirus vectors disclosed herein could be used to deliver any desired nucleic acid encoding for any desired peptide to any cell that expresses an appropriate receptor for NiV. In certain examples, these nucleic acid "payloads" will be delivered to cells expressing ephrin, for example ephrinB2 or ephrin B3. In other examples, the payload may be a nucleic acid encoding for a peptide product that is absent from the gene, such as is commonly done in gene therapy. This could be useful, for example, for targeting a genetic payload to neural stem cells. In other examples, the payload may be a nucleic acid or peptide that is toxic to the cell, for example to combat cancer cells. In other examples, the payload may be an ephrin antagonist, such as a soluble ephrinB2 or a nucleic acid capable of silencing or downregulating ephrinB2, such as an siRNA. Delivery of such ephrinB2 antagonists may be useful, for example, for impacting cell pluripotency or development, or for decreasing metastasis of certain cancer cells.

The following examples are offered to illustrate, but not to limit, the claimed embodiments. It is to be understood that the examples and embodiments described herein are for illustrative purposes only, and persons skilled in the art will recognize various parameters that can be altered without departing from the spirit of the disclosure or the scope of the appended claims.

EXAMPLES

Example 1

Generation of Truncated Glycoproteins and NiVpp Pseudotyped Lentivirus

Previous studies have shown that pseudotyping of lentiviral vectors with unmodified paramyxoviral glycoproteins is highly inefficient. In the present study, we obtained chemically-synthesized, codon-optimized wild-type NiV-F and NiV-G nucleotides. These codon-optimized NiV-F and NiV-G sequences included a tag at the 3' end encoding an AU1 peptide tag (DTYRYI) or a hemaglutinin peptide tag (YPYDVPDYA), respectively. These were subcloned into pcDNA3.1 vectors for mutagenesis. Variants of NiV-F and NiV-G were produced using a QuickChange site directed mutagenesis kit (Stratagene, Cedar Creek, Tex.) with primers designed to correspond to the desired deletions. A NiV-F variant, termed T5F or T234F, with a truncation of the cytoplasmic tail, as discussed above, was produced (see, e.g., Aguilar et al. (2007) J. Virol. 81:4520-4532). NiV-G variants were produced by making stepwise truncations of the cytoplasmic tail of NiV-G. FIG. 1 shows the variant forms of NiV-F and NiV-G that were produced.

NiVpp lentiviral vectors were created using various combinations of these variant NiV-F and NiV-G glycoproteins. All lentiviral vectors were produced by calcium phosphate-mediated transient transfection of 293 T cells. One day prior to transfection, 1.6×10$^7$ 293 T cells were seeded in a T175 flask. 7 µg of NiV-F (wild-type of variant), 7 µg of NiV-G (wild-type or variant), 12.5 µg of the packaging plasmid pCMVΔR8.9, and 12.5 µg of the lentiviral transfer vector plasmid FG12-GFP or FUhLucW were transfected into cells. After 8 h, the transfection medium was removed and fresh medium was added. 48 h post-transfection, the viral supernatant was harvested and concentrated by centrifugation at 28,000 rpm at 4° C. for 2 h over a 20% sucrose cushion. To determine viral titer, serial dilutions of concentrated viral stocks were added to 293 T cells and incubated at 37° C. for 2 h. 3 days post-infection, the cells were analyzed by flow cytometry for eGFP expression. Titers are expressed as infectious units per mL (IU/mL).

Truncation of the NiV-F cytoplasmic tail alone resulted in a titer of $\sim10^6$ IU/mL on 293 T cells, a 100-fold increase in titer compared to wtF/wtG pseudotypes (FIG. 2). With regard to the NiV-G variants, although the T234F/Δ10G and T234F/Δ25G variants demonstrated similar titers to T234F/wtG, none of the NiV-G variants produced greater titers than T234F/wtG (FIG. 2). Moreover, combinations of wt F with the NiV-G truncation variants produced extremely low titers (data not shown), indicating that truncations in NiV-F are critical for efficient pseudotyping. Following concentration, titers of $\sim10^8$-$10^9$ were obtained, compared to $10^{10}$ for VSV-G (data not shown). These high titer NiV pseudotyped lentiviruses can be used for efficient infection of ephrinB2+ cells, including for infection of hESCs, to deliver marker genes to tag ephrinB2+ hESCs, or to deliver siRNAs or other genes to antagonize the ephrinB2-ephB4 axis on hESCs.

Example 2

In Vitro and In Vivo Infection Using NiVpp Pseudotyped Lentivirus

Increasing amounts of virus (based on MOI or p24 equivalent) were added to $1\times10^5$ cells of each cell type and centrifuged at 2,000 rpm at 37° C. for 2 hours. As a specificity control, 10 nM of soluble ephrinB2 (R&D Systems) was added to the infection medium in some studies. To exclude pseudotransduction, 5 μM of nevirapine (NVP; a reverse transcriptase inhibitor) was added in some studies. For stem cell transductions, 4 ng/ml of polybrene (Sigma) was added. Following an overnight incubation with virus, the infection medium was removed and replaced with fresh medium. 72 hours post-infection, the cells were harvested and analyzed by flow cytometry for eGFP expression. For transduction of a mixed population of cells, ephrinB2+ human U87 cells were mixed with ephrinB2− non-human Chinese hamster ovary (CHO) cells at different ratios (U87:CHO ratios=1:1, 1:10, 1:100, and 1:1000), and seeded at a density of 50,000 cells per well in 24-well plates. The next day, cells were infected with 1 or 10 ng of NiV T5F/wt G, T5FΔN3/wt G, and VSV-G pseudotypes. 72 h post-infection, the cells were harvested, stained with the mouse W6/32 anti-human HLA-ABC monoclonal antibody (eBioscience), followed by Alexa 647-conjugated goat anti-mouse secondary antibodies. Samples were fixed and then analyzed by dual-color flow cytometry for human HLA and eGFP expression.

CHO, CHO-B2, and CHO-B3 cells were infected with 0.01 ng, 0.1 ng, and 1 ng (p24 equivalents) of NiVpp or VSV-Gpp lentiviral pseudotypes carrying the GFP reporter gene (FIG. 3, panels A-D). Infectivity was determined by the percent of GFP+ cells at 48 h post-infection via FACS analysis. The % GFP+ cells in each of the CHO cell lines infected by VSV-Gpp at maximal viral input (1 ng) was set at 100%, and all other infections in that cell line were normalized to this value. For reference, at 1 ng, VSV-G infected 20.2% of CHO, 22.7% of CHO-B2, and 21.6% of CHO-B3 cells. U87 cells and HMVECs were infected with T5F/wt G and T5FΔN3/wt G pseudotypes as described for panels A-C but normalized to VSV-Gpp infection of the same cell line (U87 or HMVECs) at maximal viral input (1 ng) (FIG. 3, panels E & F). For reference, at 1 ng, VSV-G infected 36.5% of U87 cells and 14.4% of HMVECs. Inhibition by 10 nM of soluble ephrinB2 (sEFN B2) was used to demonstrate specificity of NiV receptor-mediated entry. All pseudotyped particle infections, regardless of envelope used, were also abrogated by 5 μM niverapine (NVP), a reverse transcriptase inhibitor (data not shown). Data shown in FIG. 3 are averages±standard deviations for three independent experiments. Statistical analyses were performed using a two-way ANOVA with Bonferroni post-test comparison using GraphPad PRISM™. *: $p<0.05$, : $p<0.01$, **: $p<0.0001$. As this figure demonstrates, NiVpp pseudotyped lentivirus is able to effectively infect all cell types tested in an ephrinB2 dependent manner. Moreover, T5FΔN3 showed an improved infectivity versus T5F.

EphrinB2 is a functional marker of human embryonic, neural, and hematopoietic stem cells (hESC, hNSC and hHSC). To confirm that ephrinB2 is functionally expressed on hESC, hNSC and hHSC, and to confirm that T234F/wtG pseudotype can mediate transfer into these ephrinB2+ cells, we transduced human ESCs, HSCs, and NSCs with NiVpp pseudotyped lentiviruses carrying a marker gene for EGFP. FIG. 4 shows that NiV pseudotypes infected SSEA-4+ hESC (H1 line) (panel A), hNSC (Nestin+) (panel B), and a subpopulation of purified CD34+ cells from human fetal liver (panel C). More specifically, in panel A of FIG. 4, increasing amounts of NiVpp were added to H9 hESCs. Cells were stained for the cell-surface pluripotency marker, SSEA-4, and examined for GFP expression 72 h post-transduction by FACS analysis. $1\times10^8$ IU of NiVpp produced an infection rate of approximately 36% of SSEA-4+ hESC (FIG. 4, panel A). For panel B of FIG. 4, progenitor cells derived from the medial temporal lobe of a 17-week human fetus were infected with NiVpp. 72 h post-transduction, cells were stained for nestin and GFP expression was quantified by FACS analysis. The results of this analysis suggest that the NiV pseudotypes may infect NSC more efficiently than VSV-G pseudotypes. In panel C of FIG. 4, purified $CD34^+$ cells from human fetal liver were infected with NiVpp. 72 h post-transduction, cells were stained for the cell-surface marker CD34 and analyzed for GFP expression by FACS analysis. At a multiplicity of infection (MOI) of 10, T234F/wtG pseudotypes specifically transduced ~12% of purified CD34+ cells from human fetal liver. Moreover, this infection was inhibited with soluble ephrinB2 (10 nM) in all cases (data only shown for fetal liver CD34+ cells, which shows a reduction from ~12% to <1% infection in the presence of soluble ephrinB2).

In the ephrinB2+/B2− ratio study, U87 (ephrinB2+) cells were mixed with CHO (ephrinB2−) cells at different ratios (U87:CHO ratios=1:1, 1:10, 1:100, and 1:1000) and seeded at a density of 50,000 cells per well in 24-well plates. The next day, cells were infected with 1 or 10 ng of NiV T5F/wt G, T5FΔN3/wt G, and VSV-G pseudotypes. 72 h post-infection, the cells were harvested and stained with the W6/32 anti-human HLA-ABC monoclonal antibody and the infection rate (GFP-positive cells) was determined by FACS analysis. Although the cells were seeded and infected at the indicated ratio, the CHO cells divided faster and outgrew the U87 cells by about ten-fold in each sample. Data from 300,000 cells were acquired for every condition used for analysis. To take into account the differential permissivity of U87 and CHO cells to lentiviral transduction, we first calculated the "cell-specific selectivity index" for U87 cells, the U87 SI as {B/(A+B)}/{D/(C+D)} where B and D represents the % of infected (GFP+) U87 and CHO cells, respectively, and A and C represents their uninfected counterparts, such that the total fraction of U87 (A+B) and CHO (C+D) cells in any given admixture upon analysis must equal 100%. A U87 SI of >1 indicates a selective preference for infecting U87 over CHO cells. For VSV-Gpp, the U87 SI at 1 and 10 ng is 5.14 and 1.93, respectively. This likely reflects the receptor-independent preference for U87 over CHO cells due to the HIV-1 based vector backbone alone. The reduction in U87 SI at a higher inoculum of VSV-Gpp is also consistent with the known ability of VSV-G-delivered gag to saturate non-human post-entry restriction factors. Since VSV-G is not known to have a cell-type specific receptor, we calculated the "NiV receptor-specific selectivity index", or the "EphrinB2 SI" as the VSV-G or NiV Env specific U87 SI divided by the U87 SI for VSV-G. This normalizes for differences in the intrinsic permissiveness of U87 over CHO cells for lentiviral transduction. This formulation now allows one to evaluate the selectivity of NiVpp for infecting ephrinB2-expressing cells relative to VSV-Gpp under all conditions analysed. The values of the U87 SI and EphrinB2 SI for VSV-G, T5F, and T5FΔN3 pseudotypes are provided in Table 1:

TABLE 1

| Specificity Index | Infection rate | VSV-G | T5F | T5FΔN3 |
| --- | --- | --- | --- | --- |
| U87 SI | 1 ng | 5.14 | 258.7 | 292.5 |
| U87 SI | 10 ng | 1.93 | 362.8 | 342.9 |
| EphrinB2 SI | 1 ng | 1.00 | 50.3 | 56.9 |
| Ephrin B2 SI | 10 ng | 1.00 | 188.0 | 177.7 |

Figure 5:
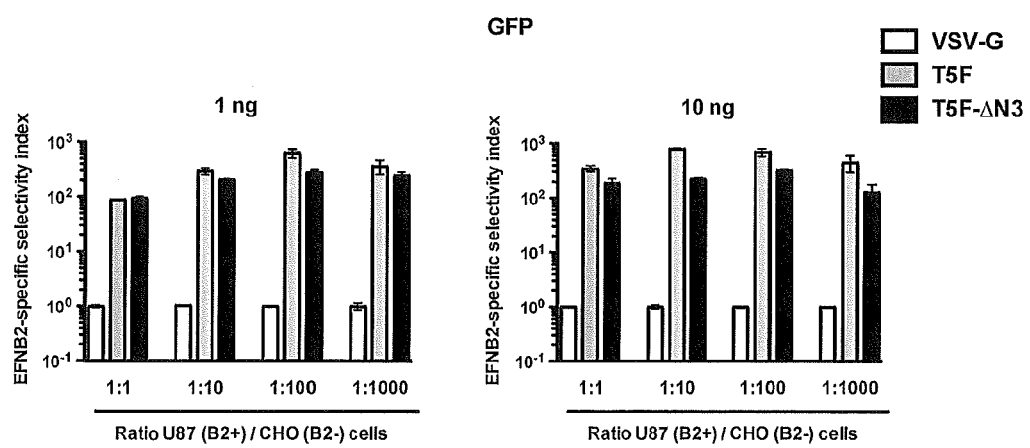
FIG. 5 shows the selectivity index of various pseudotypes of lentivirus for ephrinB2+ cells, when those cells are co-cultured with ephrinB2− cells at different ratios (1:1, 1:10, 1:100, and 1:1000).
Figure 6:
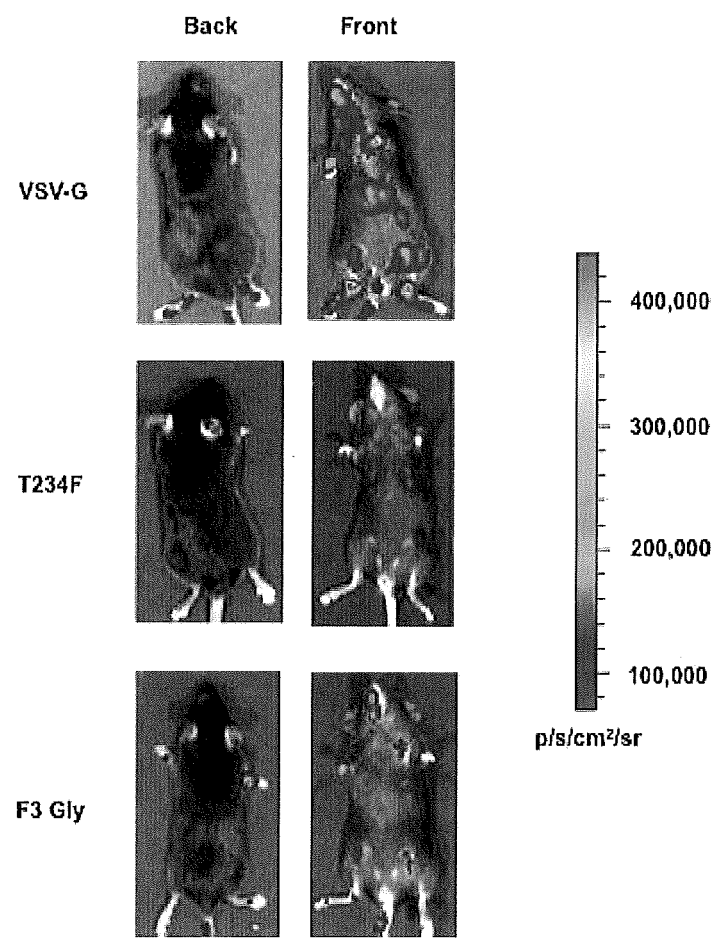
FIGS. 6 and 7 show the localization of various lentivirus pseudotypes when they are injected into the animal for an in vivo examination of infectivity.
Figure 7:
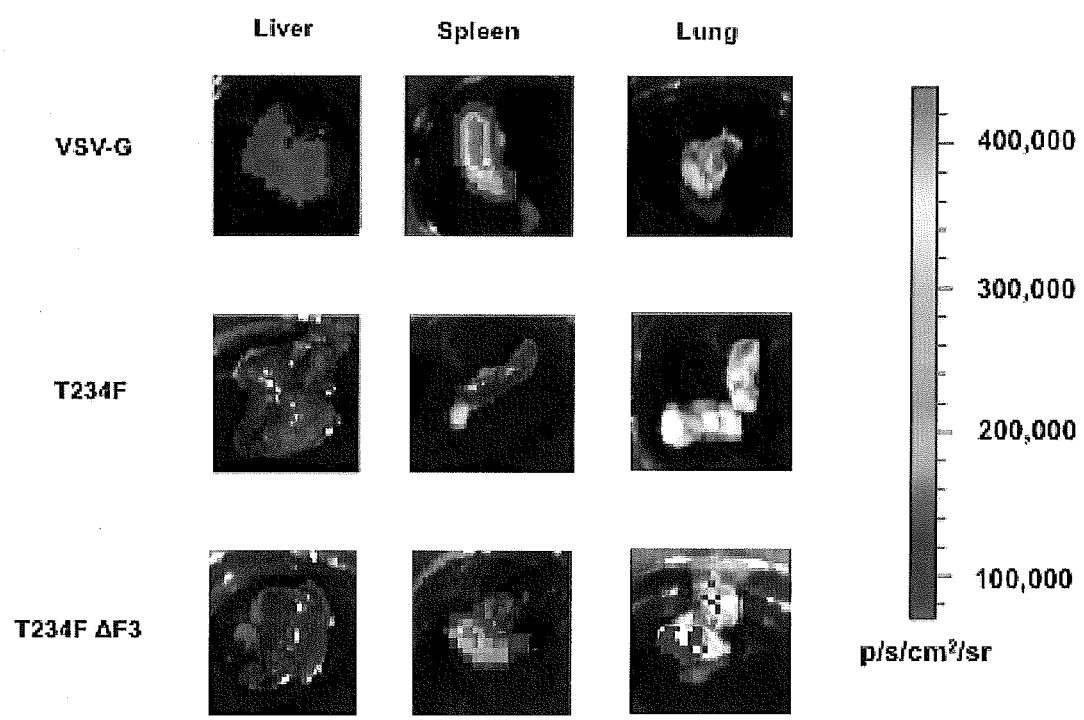

The EphrinB2 Selectivity Index calculated for VSV-Gpp, and NiVpp bearing T5F or T5F-ΔN3 for all the indicated conditions is shown in FIG. 5. Data shown are averages±standard deviations for triplicates done at 1 ng, and average±range for duplicates done at 10 ng. As these results demonstrate, the NiVpp pseudotyped lentivirus vectors have a greatly increased specificity for EphrinB2 bearing cells as compared to VSV-Gpp pseudotyped lentivirus.

For in vivo analysis, the FvcFlw (firefly luciferase) vector was pseudotyped with VSV-G and two variant NiV pseudotypes, T234F and T234FΔN3, as discussed above, as discussed above. 10 ng of p24 equivalents of each pseudotyped lentivirus was injected into C57/BL6 mice through the tail vein. At 5 days post-injection, luciferase expression was imaged. Following whole-body imaging (see FIG. 6), each organ was isolated to image luciferase expression (see FIG. 7). As the images demonstrate, the NiVpp pseudotyped lentivirus is able to avoid the liver sink and to effectively infect cells and deliver genetic payloads in other tissues.

In addition to the other publications cited throughout this application, the following references are incorporated herein in their entireties for all purposes:

1. An D S, Donahue R E, Kamata M, et al. Stable reduction of CCR5 by RNAi through hematopoietic stem cell transplant in non-human primates. Proc Natl Acad Sci USA. 2007; 104:13110-13115.
2. Shimizu S, Kamata M, Kittipongdaja P, et al. Characterization of a potent non-cytotoxic shRNA directed to the HIV-1 co-receptor CCR5. Genet Vaccines Ther. 2009; 7:8.
3. Palmer A, Klein R. Multiple roles of ephrins in morphogenesis, neuronal networking, and brain function. Genes Dev. 2003; 17:1429-1450.
4. Bowden T A, Aricescu A R, Gilbert R J, Grimes J M, Jones E Y, Stuart D I. Structural basis of Nipah and Hendra virus attachment to their cell-surface receptor ephrin-B2. Nat Struct Mol Biol. 2008; 15:567-572.
5. Graf T, Stadtfeld M. Heterogeneity of embryonic and adult stem cells. Cell Stem Cell. 2008; 3:480-483.
6. Hough S R, Laslett A L, Grimmond S B, Kolle G, Pera M F. A continuum of cell states spans pluripotency and lineage commitment in human embryonic stem cells. PLoS One. 2009; 4:e7708.
7. Kullander K, Klein R. Mechanisms and functions of Eph and ephrin signaling. Nat Rev Mol Cell Biol. 2002; 3:475-486.
8. Berges B K, Akkina S R, Folkvord J M, Connick E, Akkina R. Mucosal transmission of R5 and X4 tropic HIV-1 via vaginal and rectal routes in humanized Rag2−/− gammac −/− (RAG-hu) mice. Virology. 2008; 373:342-351.
9. Damoiseaux R, Sherman S P, Alva J A, Peterson C, Pyle A D. Integrated chemical genomics reveals modifiers of survival in human embryonic stem cells. Stem Cells. 2009; 27:533-542.
10. Pyle A D, Lock L F, Donovan P J. Neurotrophins mediate human embryonic stem cell survival. Nat Biotechnol. 2006; 24:344-350.
11. Scehnet J S, Ley E J, Krasnoperov V, et al. The role of Ephs, Ephrins, and growth factors in Kaposi sarcoma and implications of EphrinB2 blockade. Blood. 2009; 113: 254-263.
12. Fortunel N O, Otu H H, Ng H H, et al. Comment on "'Stemness': transcriptional profiling of embryonic and adult stem cells" and "a stem cell molecular signature". Science. 2003; 302:393; author reply 393.
13. Levroney E L, Aguilar H C, Fulcher J A, et al. Novel innate immune functions for galectin-1: galectin-1 inhibits cell fusion by Nipah virus envelope glycoproteins and augments dendritic cell secretion of proinflammatory cytokines. J Immunol. 2005; 175:413-420.
14. Arvanitis D, Davy A. Eph/ephrin signaling: networks. Genes Dev. 2008; 22:416-429.
15. Ng E S, Davis R P, Azzola L, Stanley E G, Elefanty A G. Forced aggregation of defined numbers of human embryonic stem cells into embryoid bodies fosters robust, reproducible hematopoietic differentiation. Blood. 2005; 106:1601-1603.

What is claimed is:

1. A Nipah virus (NiV) envelope pseudotyped lentivirus particle comprising NiV fusion (NiV-F) and attachment (NiV-G) glycoproteins, wherein the NiV-F glycoprotein has a cytoplasmic tail truncation consisting of deletion of amino acid residues 525-544 of SEQ ID NO: 1 NiV-F (T234 truncation) and a mutation to an N-linked glycosylation site, wherein the Niv-G glycoprotein is a wild type Niv-G, and wherein the lentivirus infects cells expressing Ephrin B2 or Ephrin B3 receptors.

2. The Nipah virus envelope pseudotyped lentivirus of claim 1, wherein the mutation to an N-linked glycosylation site comprises a substitution of glutamine for asparagine at amino acid position 99 of SEQ ID NO: 1 (DeltaN3 mutation).

3. A Nipah virus envelope pseudotyped lentivirus particle comprising NiV-F and NiV-G glycoproteins, wherein the NiV-F glycoprotein comprises a cytoplasmic tail truncation and a mutation to an N-linked glycosylation site and wherein the cytoplasmic tail truncation consists of deletion of amino acid residues 525-544 of SEQ ID NO: 1 NiV-F (T234 truncation), the mutation to an N-linked glycosylation site comprises a DeltaN3 mutation, and wherein the NiV-G glycoprotein is a wild type Niv-G or a truncated Niv-G selected from the group consisting of the amino acid SEQ ID NOS: 13, 15, 17, 19, 21 and 23, and wherein the lentivirus infects cells expressing Ephrin B2 or Ephrin B3 receptors.

4. The Nipah virus envelope pseudotyped lentivirus of claim 1, which exhibits about 100-fold increased viral transduction titers relative to wild type Niv-F Nipah virus envelope pseudotyped lentivirus.

5. A method for delivering a desired nucleic acid to cells which express Ephrin B2 or Ephrin B3, the method comprising contacting cells in vitro with the pseudotyped lentivirus of claim 1 or claim 3, wherein the pseudotyped lentivirus further comprises a transfer vector comprising the desired nucleic acid.

* * * * *

SEQUENCE LISTING

```
<160> NUMBER OF SEQ ID NOS: 24

<210> SEQ ID NO 1
<211> LENGTH: 546
```

```
<212> TYPE: PRT
<213> ORGANISM: Nipah virus

<400> SEQUENCE: 1

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400
```

-continued

```
Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
    530                 535                 540

Gly Thr
545

<210> SEQ ID NO 2
<211> LENGTH: 552
<212> TYPE: PRT
<213> ORGANISM: Artificial Sequence
<220> FEATURE:
<223> OTHER INFORMATION: Variant peptide

<400> SEQUENCE: 2

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
                20                  25                  30

Leu Ser Lys Ile Gly Leu Val Lys Gly Val Thr Arg Lys Tyr Lys Ile
            35                  40                  45

Lys Ser Asn Pro Leu Thr Lys Asp Ile Val Ile Lys Met Ile Pro Asn
        50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205
```

```
Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
                260                 265                 270

Ser Tyr Tyr Ile Ile Val Arg Val Tyr Phe Pro Ile Leu Thr Glu Ile
            275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
                340                 345                 350

Arg Glu Cys Leu Thr Gly Ser Thr Glu Lys Cys Pro Arg Glu Leu Val
            355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
                420                 425                 430

Leu Gly Ser Val Asn Tyr Asn Ser Glu Gly Ile Ala Ile Gly Pro Pro
            435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
                500                 505                 510

Ile Ser Phe Ile Ile Val Glu Lys Lys Arg Asn Thr Tyr Ser Arg Leu
            515                 520                 525

Glu Asp Arg Arg Val Arg Pro Thr Ser Ser Gly Asp Leu Tyr Tyr Ile
    530                 535                 540

Gly Thr Asp Thr Tyr Arg Tyr Ile
545                 550

<210> SEQ ID NO 3
<211> LENGTH: 1659
<212> TYPE: DNA
<213> ORGANISM: Artificial Sequence
<220> FEATURE:
<223> OTHER INFORMATION: Variant nucleotide

<400> SEQUENCE: 3
atggtggtga tcctggacaa gcggtgctac tgcaacctgc tgatcctgat cctgatgatc      60
```

```
agcgagtgca gcgtgggcat cctgcactac gagaagctga gcaagatcgg cctggtgaag      120
ggcgtgaccc ggaagtacaa gatcaagagc aaccccctga ccaaggacat cgtgatcaag      180
atgatcccca acgtgagcaa catgagccag tgcaccggca gcgtgatgga gaactacaag      240
acccggctga acggcatcct gaccccatc aagggcgccc tggagatcta caagaacaac       300
acccacgacc tggtgggcga cgtgcggctg ccggcgtga tcatggccgg cgtggccatc       360
ggcatcgcca cagccgccca gatcaccgcc ggagtggccc tgtacgaggc catgaagaac      420
gccgacaaca tcaacaagct gaagagcagc atcgagagcc caacgaggc cgtggtgaag       480
ctgcaggaga ccgccgagaa accgtgtac gtgctgaccg ccctgcagga ctacatcaac       540
accaacctgg tgcccaccat cgacaagatc agctgcaagc agaccgagct gagcctggac      600
ctggccctga gcaagtacct gagcgacctg ctgttcgtgt tcggccccaa cctgcaggac      660
cccgtgagca acagcatgac catccaggcc atcagccagg ccttcggcgg caactacgag      720
accctgctgc ggaccctggg ctacgccacc gaggacttcg acgacctgct ggagagcgac      780
agcatcaccg ccagatcat ctacgtggac ctgagcagct actacatcat cgtgcgggtg       840
tacttcccca tcctgaccga gatccagcag gcctacatcc aggagctgct gcccgtgagc      900
ttcaacaacg acaacagcga gtggatcagc atcgtgccca acttcatcct ggtgcggaac      960
accctgatca gcaacatcga gatcggcttc tgcctgatca ccaagcggag cgtgatctgc     1020
aaccaggact acgccacccc catgaccaac aacatgcggg agtgcctgac cggcagcacc     1080
gagaagtgcc caggagct ggtggtgagc agccacgtgc ccggttcgc cctgagcaac        1140
ggcgtgctgt cgccaactg catcagcgtg acctgccagt gccagaccac cggcagagcc     1200
atcagccaga gcggcgagca gaccctgctg atgatcgaca acaccacctg ccccaccgcc     1260
gtgctgggca acgtgatcat cagcctgggc aagtatctgg gcagcgtgaa ctacaacagc     1320
gagggcatcg ccatcggccc tcccgtgttc accgacaagg tggacatcag cagccagatc     1380
agcagcatga accagagcct gcagcagagc aaggattaca tcaaggaggc ccagcggctg     1440
ctggacaccg tgaaccccag cctgatcagc atgctgtcca tgatcatcct gtacgtgctg     1500
agcatcgcca gcctgtgcat cggcctgatc accttcatca gcttcatcat cgtggagaag     1560
aagcggaaca cctacagccg gctggaggac cggcgggtgc ggcccaccag cagcggcgac     1620
ctgtactaca tcggcaccga cacctaccgg tacatctaa                            1659
```

<210> SEQ ID NO 4
<211> LENGTH: 532
<212> TYPE: PRT
<213> ORGANISM: Artificial Sequence
<220> FEATURE:
<223> OTHER INFORMATION: Variant peptide

<400> SEQUENCE: 4

```
Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Lys Met Ile Pro Asn
    50                  55                  60

Val Ser Asn Met Ser Gln Cys Thr Gly Ser Val Met Glu Asn Tyr Lys
65                  70                  75                  80
```

-continued

```
Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495
```

Leu Tyr Val Leu Ser Ile Ala Ser Leu Cys Ile Gly Leu Ile Thr Phe
                500                 505                 510

Ile Ser Phe Ile Ile Val Glu Lys Lys Arg Asn Thr Gly Thr Asp Thr
        515                 520                 525

Tyr Arg Tyr Ile
    530

<210> SEQ ID NO 5
<211> LENGTH: 1599
<212> TYPE: DNA
<213> ORGANISM: Artificial Sequence
<220> FEATURE:
<223> OTHER INFORMATION: Variant nucleotide

<400> SEQUENCE: 5

| | | | | | |
|---|---|---|---|---|---|
| atggtggtga | tcctggacaa | gcggtgctac | tgcaacctgc | tgatcctgat | cctgatgatc | 60 |
| agcgagtgca | gcgtgggcat | cctgcactac | gagaagctga | gcaagatcgg | cctggtgaag | 120 |
| ggcgtgaccc | ggaagtacaa | gatcaagagc | aaccccctga | ccaaggacat | cgtgatcaag | 180 |
| atgatcccca | acgtgagcaa | catgagccag | tgcaccggca | gcgtgatgga | gaactacaag | 240 |
| acccggctga | acggcatcct | gacccccatc | aagggcgccc | tggagatcta | caagaacaac | 300 |
| acccacgacc | tggtgggcga | cgtgcggctg | gccgcgtga | tcatggccgg | cgtggccatc | 360 |
| ggcatcgcca | gcgcgccca | gatcaccgcc | ggagtggccc | tgtacgaggc | catgaagaac | 420 |
| gccgacaaca | tcaacaagct | gaagagcagc | atcgagagca | ccaacgaggc | cgtggtgaag | 480 |
| ctgcaggaga | ccgccgagaa | accgtgtac | gtgctgaccg | ccctgcagga | ctacatcaac | 540 |
| accaacctgg | tgcccaccat | cgacaagatc | agctgcaagc | agaccgagct | gagcctggac | 600 |
| ctggccctga | gcaagtacct | gagcgacctg | ctgttcgtgt | tcggccccaa | cctgcaggac | 660 |
| cccgtgagca | acagcatgac | catccaggcc | atcagccagg | ccttcggcgg | caactacgag | 720 |
| accctgctgc | ggaccctggg | ctacgccacc | gaggacttcg | acgacctgct | ggagagcgac | 780 |
| agcatcaccg | ccagatcat | ctacgtggac | ctgagcagct | actacatcat | cgtgcgggtg | 840 |
| tacttcccca | tcctgaccga | gatccagcag | gcctacatcc | aggagctgct | gcccgtgagc | 900 |
| ttcaacaacg | acaacagcga | gtggatcagc | atcgtgccca | cttcatcct | ggtgcggaac | 960 |
| accctgatca | gcaacatcga | gatcggcttc | tgcctgatca | ccaagcggag | cgtgatctgc | 1020 |
| aaccaggact | acgccacccc | catgaccaac | aacatgcggg | agtgcctgac | cggcagcacc | 1080 |
| gagaagtgcc | ccagggagct | ggtggtgagc | agccacgtgc | ccggttcgc | cctgagcaac | 1140 |
| ggcgtgctgt | cgccaactg | catcagcgtg | acctgccagt | gccagaccac | cggcagagcc | 1200 |
| atcagccaga | gcggcgagca | gaccctgctg | atgatcgaca | acaccacctg | ccccaccgcc | 1260 |
| gtgctgggca | acgtgatcat | cagcctgggc | aagtatctgg | gcagcgtgaa | ctacaacagc | 1320 |
| gagggcatcg | ccatcggccc | tcccgtgttc | accgacaagg | tggacatcag | cagccagatc | 1380 |
| agcagcatga | accagagcct | gcagcagagc | aaggattaca | tcaaggaggc | ccagcggctg | 1440 |
| ctggacaccg | tgaaccccag | cctgatcagc | atgctgtcca | tgatcatcct | gtacgtgctg | 1500 |
| agcatcgcca | gcctgtgcat | cggcctgatc | accttcatca | gcttcatcat | cgtggagaag | 1560 |
| aagcggaaca | ccggcaccga | cacctaccgg | tacatctaa | | | 1599 |

<210> SEQ ID NO 6
<211> LENGTH: 552
<212> TYPE: PRT
<213> ORGANISM: Artificial Sequence
<220> FEATURE:

<223> OTHER INFORMATION: Variant peptide

<400> SEQUENCE: 6

```
Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Gln Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400
```

```
Ile Ser Gln Ser Gly Glu Gln Thr Leu Leu Met Ile Asp Asn Thr Thr
            405                 410                 415
Cys Pro Thr Ala Val Leu Gly Asn Val Ile Ile Ser Leu Gly Lys Tyr
            420                 425                 430
Leu Gly Ser Val Asn Tyr Asn Ser Glu Gly Ile Ala Ile Gly Pro Pro
            435                 440                 445
Val Phe Thr Asp Lys Val Asp Ile Ser Ser Gln Ile Ser Ser Met Asn
            450                 455                 460
Gln Ser Leu Gln Gln Ser Lys Asp Tyr Ile Lys Glu Ala Gln Arg Leu
465                 470                 475                 480
Leu Asp Thr Val Asn Pro Ser Leu Ile Ser Met Leu Ser Met Ile Ile
            485                 490                 495
Leu Tyr Val Leu Ser Ile Ala Ser Leu Cys Ile Gly Leu Ile Thr Phe
            500                 505                 510
Ile Ser Phe Ile Ile Val Glu Lys Lys Arg Asn Thr Tyr Ser Arg Leu
            515                 520                 525
Glu Asp Arg Arg Val Arg Pro Thr Ser Ser Gly Asp Leu Tyr Tyr Ile
            530                 535                 540
Gly Thr Asp Thr Tyr Arg Tyr Ile
545                 550
```

<210> SEQ ID NO 7
<211> LENGTH: 1659
<212> TYPE: DNA
<213> ORGANISM: Artificial Sequence
<220> FEATURE:
<223> OTHER INFORMATION: Variant nucleotide

<400> SEQUENCE: 7

```
atggtggtga tcctggacaa gcggtgctac tgcaacctgc tgatcctgat cctgatgatc      60
agcgagtgca gcgtgggcat cctgcactac gagaagctga gcaagatcgg cctggtgaag     120
ggcgtgaccc ggaagtacaa gatcaagagc aaccccctga ccaaggacat cgtgatcaag     180
atgatcccca cgtgagcaa catgagccag tgcaccggca gcgtgatgga aactacaag       240
acccggctga cggcatcct gaccccatc aagggcgccc tggagatcta caagcaraac       300
acccacgacc tggtgggcga cgtgcggctg ccggcgtga tcatggccgg cgtggccatc     360
ggcatcgcca gccgcccca gatcaccgcc ggagtggccc tgtacgaggc catgaagaac     420
gccgacaaca tcaacaagct gaagagcagc atcgagagca ccaacgaggc cgtggtgaag    480
ctgcaggaga ccgccgagaa accgtgtac gtgctgaccg ccctgcagga ctacatcaac     540
accaacctgg tgcccaccat cgacaagatc agctgcaagc agaccgagct gagcctggac    600
ctggccctga gcaagtacct gagcgacctg ctgttcgtgt cggccccaa cctgcaggac     660
cccgtgagca acagcatgac catccaggcc atcagccagg ccttcggcgg caactacgag    720
accctgctgc ggaccctggg ctacgccacc gaggacttcg acgacctgct ggagagcgac   780
agcatcaccg ccagatcat ctacgtggac ctgagcagct actacatcat cgtgcgggtg    840
tacttcccca tcctgaccga gatccagcag gcctacatcc aggagctgct gcccgtgagc   900
ttcaacaacg acaacagcga gtggatcagc atcgtgccca acttcatcct ggtgcggaac    960
accctgatca gcaacatcga gatcggcttc tgcctgatca ccaagcggag cgtgatctgc   1020
aaccaggact acgccacccc catgaccaac aacatgcggg agtgcctgac cggcagcacc   1080
gagaagtgcc ccagggagct ggtggtgagc agccacgtgc ccggttcgc cctgagcaac    1140
ggcgtgctgt cgccaactg catcagcgtg acctgccagt gccagaccac cggcagagcc   1200
```

-continued

```
atcagccaga gcggcgagca gaccctgctg atgatcgaca acaccacctg ccccaccgcc    1260
gtgctgggca acgtgatcat cagcctgggc aagtatctgg gcagcgtgaa ctacaacagc    1320
gagggcatcg ccatcggccc tcccgtgttc accgacaagg tggacatcag cagccagatc    1380
agcagcatga accagagcct gcagcagagc aaggattaca tcaaggaggc ccagcggctg    1440
ctggacaccg tgaacccag cctgatcagc atgctgtcca tgatcatcct gtacgtgctg    1500
agcatcgcca gcctgtgcat cggcctgatc accttcatca gcttcatcat cgtggagaag    1560
aagcggaaca cctacagccg gctggaggac cggcgggtgc ggcccaccag cagcggcgac    1620
ctgtactaca tcggcaccga cacctaccgg tacatctaa                           1659
```

<210> SEQ ID NO 8
<211> LENGTH: 532
<212> TYPE: PRT
<213> ORGANISM: Artificial Sequence
<220> FEATURE:
<223> OTHER INFORMATION: Variant peptide

<400> SEQUENCE: 8

```
Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Gln Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270
```

```
Ser Tyr Tyr Ile Ile Val Arg Val Tyr Phe Pro Ile Leu Thr Glu Ile
            275                 280                 285

Gln Gln Ala Tyr Ile Gln Glu Leu Leu Pro Val Ser Phe Asn Asn Asp
        290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Gly Thr Asp Thr
        515                 520                 525

Tyr Arg Tyr Ile
    530

<210> SEQ ID NO 9
<211> LENGTH: 1599
<212> TYPE: DNA
<213> ORGANISM: Artificial Sequence
<220> FEATURE:
<223> OTHER INFORMATION: Variant nucleotide

<400> SEQUENCE: 9
atggtggtga tcctggacaa gcggtgctac tgcaacctgc tgatcctgat cctgatgatc    60
agcgagtgca gcgtgggcat cctgcactac gagaagctga gcaagatcgg cctggtgaag   120
ggcgtgaccc ggaagtacaa gatcaagagc aaccccctga ccaaggacat cgtgatcaag   180
atgatcccca acgtgagcaa catgagccag tgcaccggca gcgtgatgga gaactacaag   240
acccggctga acggcatcct gacccccatc aagggcgccc tggagatcta caagcaraac   300
acccacgacc tggtgggcga cgtgcggctg gccggcgtga tcatggccgg cgtggccatc   360
ggcatcgcca cagccgccca gatcaccgcc ggagtggccc tgtacgaggc catgaagaac   420
gccgacaaca tcaacaagct gaagagcagc atcgagagca ccaacgaggc cgtggtgaag   480
ctgcaggaga ccgccgagaa aaccgtgtac gtgctgaccg ccctgcagga ctacatcaac   540
```

```
accaacctgg tgcccaccat cgacaagatc agctgcaagc agaccgagct gagcctggac    600
ctggccctga gcaagtacct gagcgacctg ctgttcgtgt cggccccaa cctgcaggac     660 cccgtgagca acagcatgac catccaggcc atcagccagg ccttcggcgg caactacgag    720
accctgctgc ggaccctggg ctacgccacc gaggacttcg acgacctgct ggagagcgac    780
agcatcaccg gccagatcat ctacgtggac ctgagcagct actacatcat cgtgcgggtg    840
tacttcccca tcctgaccga gatccagcag gcctacatcc aggagctgct gcccgtgagc    900
ttcaacaacg acaacagcga gtggatcagc atcgtgccca acttcatcct ggtgcggaac    960
accctgatca gcaacatcga gatcggcttc tgcctgatca ccaagcggag cgtgatctgc   1020
aaccaggact acgccacccc catgaccaac aacatgcggg agtgcctgac cggcagcacc   1080
gagaagtgcc ccagggagct ggtggtgagc agccacgtgc cccggttcgc cctgagcaac   1140
ggcgtgctgt tcgccaactg catcagcgtg acctgccagt gccagaccac cggcagagcc   1200
atcagccaga gcggcgagca gaccctgctg atgatcgaca caccacctg ccccaccgcc    1260 gtgctgggca acgtgatcat cagcctgggc aagtatctgg gcagcgtgaa ctacaacagc   1320
gagggcatcg ccatcggccc tcccgtgttc accgacaagg tggacatcag cagccagatc   1380
agcagcatga accagagcct gcagcagagc aaggattaca tcaaggaggc ccagcggctg   1440
ctggacaccg tgaaccccag cctgatcagc atgctgtcca tgatcatcct gtacgtgctg   1500
agcatcgcca gcctgtgcat cggcctgatc accttcatca gcttcatcat cgtggagaag   1560
aagcggaaca ccggcaccga cacctaccgg tacatctaa                          1599
```

<210> SEQ ID NO 10
<211> LENGTH: 602
<212> TYPE: PRT
<213> ORGANISM: Nipah virus

<400> SEQUENCE: 10

```
Met Gly Pro Ala Glu Asn Lys Lys Val Arg Phe Glu Asn Thr Thr Ser
1               5                   10                  15

Asp Lys Gly Lys Ile Pro Ser Lys Val Ile Lys Ser Tyr Tyr Gly Thr
                20                  25                  30

Met Asp Ile Lys Lys Ile Asn Glu Gly Leu Leu Asp Ser Lys Ile Leu
            35                  40                  45

Ser Ala Phe Asn Thr Val Ile Ala Leu Leu Gly Ser Ile Val Ile Ile
        50                  55                  60

Val Met Asn Ile Met Ile Ile Gln Asn Tyr Thr Arg Ser Thr Asp Asn
65                  70                  75                  80

Gln Ala Val Ile Lys Asp Ala Leu Gln Gly Ile Gln Gln Ile Lys
                85                  90                  95

Gly Leu Ala Asp Lys Ile Gly Thr Glu Ile Gly Pro Lys Val Ser Leu
                100                 105                 110

Ile Asp Thr Ser Ser Thr Ile Thr Ile Pro Ala Asn Ile Gly Leu Leu
            115                 120                 125

Gly Ser Lys Ile Ser Gln Ser Thr Ala Ser Ile Asn Glu Asn Val Asn
        130                 135                 140

Glu Lys Cys Lys Phe Thr Leu Pro Pro Leu Lys Ile His Glu Cys Asn
145                 150                 155                 160

Ile Ser Cys Pro Asn Pro Leu Pro Phe Arg Glu Tyr Arg Pro Gln Thr
                165                 170                 175

Glu Gly Val Ser Asn Leu Val Gly Leu Pro Asn Asn Ile Cys Leu Gln
            180                 185                 190
```

```
Lys Thr Ser Asn Gln Ile Leu Lys Pro Lys Leu Ile Ser Tyr Thr Leu
    195                 200                 205

Pro Val Val Gly Gln Ser Gly Thr Cys Ile Thr Asp Pro Leu Leu Ala
210                 215                 220

Met Asp Glu Gly Tyr Phe Ala Tyr Ser His Leu Glu Arg Ile Gly Ser
225                 230                 235                 240

Cys Ser Arg Gly Val Ser Lys Gln Arg Ile Ile Gly Val Gly Glu Val
                245                 250                 255

Leu Asp Arg Gly Asp Glu Val Pro Ser Leu Phe Met Thr Asn Val Trp
                260                 265                 270

Thr Pro Pro Asn Pro Asn Thr Val Tyr His Cys Ser Ala Val Tyr Asn
        275                 280                 285

Asn Glu Phe Tyr Tyr Val Leu Cys Ala Val Ser Thr Val Gly Asp Pro
        290                 295                 300

Ile Leu Asn Ser Thr Tyr Trp Ser Gly Ser Leu Met Met Thr Arg Leu
305                 310                 315                 320

Ala Val Lys Pro Lys Ser Asn Gly Gly Tyr Asn Gln His Gln Leu
                325                 330                 335

Ala Leu Arg Ser Ile Glu Lys Gly Arg Tyr Asp Lys Val Met Pro Tyr
                340                 345                 350

Gly Pro Ser Gly Ile Lys Gln Gly Asp Thr Leu Tyr Phe Pro Ala Val
                355                 360                 365

Gly Phe Leu Val Arg Thr Glu Phe Lys Tyr Asn Asp Ser Asn Cys Pro
                370                 375                 380

Ile Thr Lys Cys Gln Tyr Ser Lys Pro Glu Asn Cys Arg Leu Ser Met
385                 390                 395                 400

Gly Ile Arg Pro Asn Ser His Tyr Ile Leu Arg Ser Gly Leu Leu Lys
                405                 410                 415

Tyr Asn Leu Ser Asp Gly Glu Asn Pro Lys Val Val Phe Ile Glu Ile
                420                 425                 430

Ser Asp Gln Arg Leu Ser Ile Gly Ser Pro Ser Lys Ile Tyr Asp Ser
                435                 440                 445

Leu Gly Gln Pro Val Phe Tyr Gln Ala Ser Phe Ser Trp Asp Thr Met
                450                 455                 460

Ile Lys Phe Gly Asp Val Leu Thr Val Asn Pro Leu Val Val Asn Trp
465                 470                 475                 480

Arg Asn Asn Thr Val Ile Ser Arg Pro Gly Gln Ser Gln Cys Pro Arg
                485                 490                 495

Phe Asn Thr Cys Pro Glu Ile Cys Trp Glu Gly Val Tyr Asn Asp Ala
                500                 505                 510

Phe Leu Ile Asp Arg Ile Asn Trp Ile Ser Ala Gly Val Phe Leu Asp
                515                 520                 525

Ser Asn Gln Thr Ala Glu Asn Pro Val Phe Thr Val Phe Lys Asp Asn
530                 535                 540

Glu Ile Leu Tyr Arg Ala Gln Leu Ala Ser Glu Asp Thr Asn Ala Gln
545                 550                 555                 560

Lys Thr Ile Thr Asn Cys Phe Leu Leu Lys Asn Lys Ile Trp Cys Ile
                565                 570                 575

Ser Leu Val Glu Ile Tyr Asp Thr Gly Asp Asn Val Ile Arg Pro Lys
                580                 585                 590

Leu Phe Ala Val Lys Ile Pro Glu Gln Cys
                595                 600
```

```
<210> SEQ ID NO 11
<211> LENGTH: 611
<212> TYPE: PRT
<213> ORGANISM: Artificial Sequence
<220> FEATURE:
<223> OTHER INFORMATION: Variant peptide

<400> SEQUENCE: 11

Met Gly Pro Ala Glu Asn Lys Lys Val Arg Phe Glu Asn Thr Thr Ser
1               5                   10                  15

Asp Lys Gly Lys Ile Pro Ser Lys Val Ile Lys Ser Tyr Tyr Gly Thr
            20                  25                  30

Met Asp Ile Lys Lys Ile Asn Glu Gly Leu Leu Asp Ser Lys Ile Leu
        35                  40                  45

Ser Ala Phe Asn Thr Val Ile Ala Leu Leu Gly Ser Ile Val Ile Ile
    50                  55                  60

Val Met Asn Ile Met Ile Ile Gln Asn Tyr Thr Arg Ser Thr Asp Asn
65                  70                  75                  80

Gln Ala Val Ile Lys Asp Ala Leu Gln Gly Ile Gln Gln Ile Lys
                85                  90                  95

Gly Leu Ala Asp Lys Ile Gly Thr Glu Ile Gly Pro Lys Val Ser Leu
            100                 105                 110

Ile Asp Thr Ser Ser Thr Ile Thr Ile Pro Ala Asn Ile Gly Leu Leu
        115                 120                 125

Gly Ser Lys Ile Ser Gln Ser Thr Ala Ser Ile Asn Glu Asn Val Asn
    130                 135                 140

Glu Lys Cys Lys Phe Thr Leu Pro Pro Leu Lys Ile His Glu Cys Asn
145                 150                 155                 160

Ile Ser Cys Pro Asn Pro Leu Pro Phe Arg Glu Tyr Arg Pro Gln Thr
                165                 170                 175

Glu Gly Val Ser Asn Leu Val Gly Leu Pro Asn Asn Ile Cys Leu Gln
            180                 185                 190

Lys Thr Ser Asn Gln Ile Leu Lys Pro Lys Leu Ile Ser Tyr Thr Leu
        195                 200                 205

Pro Val Val Gly Gln Ser Gly Thr Cys Ile Thr Asp Pro Leu Leu Ala
    210                 215                 220

Met Asp Glu Gly Tyr Phe Ala Tyr Ser His Leu Glu Arg Ile Gly Ser
225                 230                 235                 240

Cys Ser Arg Gly Val Ser Lys Gln Arg Ile Ile Gly Val Gly Glu Val
                245                 250                 255

Leu Asp Arg Gly Asp Glu Val Pro Ser Leu Phe Met Thr Asn Val Trp
            260                 265                 270

Thr Pro Pro Asn Pro Asn Thr Val Tyr His Cys Ser Ala Val Tyr Asn
        275                 280                 285

Asn Glu Phe Tyr Tyr Val Leu Cys Ala Val Ser Thr Val Gly Asp Pro
    290                 295                 300

Ile Leu Asn Ser Thr Tyr Trp Ser Gly Ser Leu Met Met Thr Arg Leu
305                 310                 315                 320

Ala Val Lys Pro Lys Ser Asn Gly Gly Tyr Asn Gln His Gln Leu
                325                 330                 335

Ala Leu Arg Ser Ile Glu Lys Gly Arg Tyr Asp Lys Val Met Pro Tyr
            340                 345                 350

Gly Pro Ser Gly Ile Lys Gln Gly Asp Thr Leu Tyr Phe Pro Ala Val
        355                 360                 365
```

Gly Phe Leu Val Arg Thr Glu Phe Lys Tyr Asn Asp Ser Asn Cys Pro
370                 375                 380

Ile Thr Lys Cys Gln Tyr Ser Lys Pro Glu Asn Cys Arg Leu Ser Met
385                 390                 395                 400

Gly Ile Arg Pro Asn Ser His Tyr Ile Leu Arg Ser Gly Leu Leu Lys
                405                 410                 415

Tyr Asn Leu Ser Asp Gly Glu Asn Pro Lys Val Val Phe Ile Glu Ile
                420                 425                 430

Ser Asp Gln Arg Leu Ser Ile Gly Ser Pro Ser Lys Ile Tyr Asp Ser
                435                 440                 445

Leu Gly Gln Pro Val Phe Tyr Gln Ala Ser Phe Ser Trp Asp Thr Met
450                 455                 460

Ile Lys Phe Gly Asp Val Leu Thr Val Asn Pro Leu Val Val Asn Trp
465                 470                 475                 480

Arg Asn Asn Thr Val Ile Ser Arg Pro Gly Gln Ser Gln Cys Pro Arg
                485                 490                 495

Phe Asn Thr Cys Pro Glu Ile Cys Trp Glu Gly Val Tyr Asn Asp Ala
                500                 505                 510

Phe Leu Ile Asp Arg Ile Asn Trp Ile Ser Ala Gly Val Phe Leu Asp
                515                 520                 525

Ser Asn Gln Thr Ala Glu Asn Pro Val Phe Thr Val Phe Lys Asp Asn
530                 535                 540

Glu Ile Leu Tyr Arg Ala Gln Leu Ala Ser Glu Asp Thr Asn Ala Gln
545                 550                 555                 560

Lys Thr Ile Thr Asn Cys Phe Leu Leu Lys Asn Lys Ile Trp Cys Ile
                565                 570                 575

Ser Leu Val Glu Ile Tyr Asp Thr Gly Asp Asn Val Ile Arg Pro Lys
                580                 585                 590

Leu Phe Ala Val Lys Ile Pro Glu Gln Cys Tyr Pro Tyr Asp Val Pro
                595                 600                 605

Asp Tyr Ala
    610

<210> SEQ ID NO 12
<211> LENGTH: 1836
<212> TYPE: DNA
<213> ORGANISM: Artificial Sequence
<220> FEATURE:
<223> OTHER INFORMATION: Variant nucleotide

<400> SEQUENCE: 12
atgggacctg ccgagaacaa gaaagtgcgg ttcgagaaca ccacaagcga caagggcaag     60
atccccagca agtgatcaa gagctactac ggcaccatgg acatcaagaa gatcaacgag    120
ggcctgctgg acagcaagat cctgagcgcc ttcaacaccg tgatcgccct gctgggcagc    180
atcgtgatca ttgtgatgaa catcatgatc atccagaact acaccggag caccgacaac    240 caggccgtga tcaaggacgc cctgcaggga tccagcagc agatcaaggg cctggccgac    300
aagatcggca ccgagatcgg ccccaaagtg agcctgatcg acaccagcag caccatcacc    360
atccccgcca catcggcct gctgggatcc aagatcagcc agagcaccgc cagcatcaac    420
gagaacgtga acgagaagtg caagttcacc ctgccccccc tgaagatcca cgagtgcaac    480
atcagctgcc ccaaccccct gcccttccgg gagtaccggc ccagaccga gggcgtgagc    540 aacctggtgg gcctgcccaa caacatctgc ctgcagaaaa ccagcaacca gatcctgaag    600
cccaagctga tctcctacac cctgcccgtg gtgggccaga gcggcacctg catcaccgac    660

```
cccctgctgg ccatggacga gggctacttc gcctacagcc acctggagcg atcggcagc    720
tgcagccggg gagtgagcaa gcagcggatc atcggcgtgg gcgaagtgct ggaccgggc    780
gacgaagtgc ccagcctgtt catgaccaac gtgtggaccc ccccaaccc caacaccgtg    840
taccactgca gcgccgtgta caacaacgag ttctactacg tgctgtgcgc cgtgagcacc    900
gtgggcgacc ccatcctgaa cagcacctac tggagcggca gcctgatgat gacccggctg    960
gccgtgaagc taagagcaa cggcggaggc tacaaccagc accagctggc cctgcggagc   1020
atcgagaagg gccggtacga caaagtgatg ccctacggcc cagcggcat caagcagggc   1080
gacacccctgt acttccccgc cgtgggcttc ctggtgcgga ccgagttcaa gtacaacgac   1140
agcaactgcc ccatcaccaa gtgccagtac agcaagcccg agaactgccg gctgagcatg   1200
ggcatccggc ccaacagcca ctacatcctg cggagcggcc tgctgaagta caacctgagc   1260
gacggcgaga accccaaagt ggtgttcatc gagatcagcg accagagact gagcatcggc   1320
agccccagca agatctacga cagcctgggc cagcccgtgt ctaccaggcc agcttcagc    1380
tgggacacca tgatcaagtt cggcgacgtg ctgaccgtga accccctggt ggtgaactgg   1440
cggaacaata ccgtgatcag cagacccggc cagagccagt gccccggtt caacacctgc   1500
cccgagatct gctgggaggg cgtgtacaac gacgccttcc tgatcgaccg gatcaactgg   1560
atcagcgccg gagtgttcct ggatagcaac cagaccgccg agaatcccgt gttcaccgtg   1620
tttaaggaca acgagatcct gtacagagcc cagctggcca gcgaggacac caacgcccag   1680
aaaaccatca ccaactgctt cctgctgaag aataagatct ggtgcatcag cctggtggag   1740
atctacgata ccggcgacaa cgtgatcagg cccaagctgt cgccgtgaa gatccccgag    1800
cagtgctacc cctacgacgt gcccgactac gcctga                             1836

<210> SEQ ID NO 13
<211> LENGTH: 606
<212> TYPE: PRT
<213> ORGANISM: Artificial Sequence
<220> FEATURE:
<223> OTHER INFORMATION: Variant peptide

<400> SEQUENCE: 13

Met Gly Lys Val Arg Phe Glu Asn Thr Thr Ser Asp Lys Gly Lys Ile
1               5                   10                  15

Pro Ser Lys Val Ile Lys Ser Tyr Tyr Gly Thr Met Asp Ile Lys Lys
            20                  25                  30

Ile Asn Glu Gly Leu Leu Asp Ser Lys Ile Leu Ser Ala Phe Asn Thr
        35                  40                  45

Val Ile Ala Leu Leu Gly Ser Ile Val Ile Val Met Asn Ile Met
    50                  55                  60

Ile Ile Gln Asn Tyr Thr Arg Ser Thr Asp Asn Gln Ala Val Ile Lys
65                  70                  75                  80

Asp Ala Leu Gln Gly Ile Gln Gln Gln Ile Lys Gly Leu Ala Asp Lys
                85                  90                  95

Ile Gly Thr Glu Ile Gly Pro Lys Val Ser Leu Ile Asp Thr Ser Ser
            100                 105                 110

Thr Ile Thr Ile Pro Ala Asn Ile Gly Leu Leu Gly Ser Lys Ile Ser
        115                 120                 125

Gln Ser Thr Ala Ser Ile Asn Glu Asn Val Asn Glu Lys Cys Lys Phe
    130                 135                 140
```

```
Thr Leu Pro Pro Leu Lys Ile His Glu Cys Asn Ile Ser Cys Pro Asn
145                 150                 155                 160

Pro Leu Pro Phe Arg Glu Tyr Arg Pro Gln Thr Glu Gly Val Ser Asn
            165                 170                 175

Leu Val Gly Leu Pro Asn Asn Ile Cys Leu Gln Lys Thr Ser Asn Gln
        180                 185                 190

Ile Leu Lys Pro Lys Leu Ile Ser Tyr Thr Leu Pro Val Val Gly Gln
    195                 200                 205

Ser Gly Thr Cys Ile Thr Asp Pro Leu Leu Ala Met Asp Glu Gly Tyr
210                 215                 220

Phe Ala Tyr Ser His Leu Glu Arg Ile Gly Ser Cys Ser Arg Gly Val
225                 230                 235                 240

Ser Lys Gln Arg Ile Ile Gly Val Gly Glu Val Leu Asp Arg Gly Asp
                245                 250                 255

Glu Val Pro Ser Leu Phe Met Thr Asn Val Trp Thr Pro Pro Asn Pro
            260                 265                 270

Asn Thr Val Tyr His Cys Ser Ala Val Tyr Asn Asn Glu Phe Tyr Tyr
            275                 280                 285

Val Leu Cys Ala Val Ser Thr Val Gly Asp Pro Ile Leu Asn Ser Thr
290                 295                 300

Tyr Trp Ser Gly Ser Leu Met Met Thr Arg Leu Ala Val Lys Pro Lys
305                 310                 315                 320

Ser Asn Gly Gly Gly Tyr Asn Gln His Gln Leu Ala Leu Arg Ser Ile
                325                 330                 335

Glu Lys Gly Arg Tyr Asp Lys Val Met Pro Tyr Gly Pro Ser Gly Ile
            340                 345                 350

Lys Gln Gly Asp Thr Leu Tyr Phe Pro Ala Val Gly Phe Leu Val Arg
            355                 360                 365

Thr Glu Phe Lys Tyr Asn Asp Ser Asn Cys Pro Ile Thr Lys Cys Gln
            370                 375                 380

Tyr Ser Lys Pro Glu Asn Cys Arg Leu Ser Met Gly Ile Arg Pro Asn
385                 390                 395                 400

Ser His Tyr Ile Leu Arg Ser Gly Leu Leu Lys Tyr Asn Leu Ser Asp
                405                 410                 415

Gly Glu Asn Pro Lys Val Val Phe Ile Glu Ile Ser Asp Gln Arg Leu
            420                 425                 430

Ser Ile Gly Ser Pro Ser Lys Ile Tyr Asp Ser Leu Gly Gln Pro Val
            435                 440                 445

Phe Tyr Gln Ala Ser Phe Ser Trp Asp Thr Met Ile Lys Phe Gly Asp
450                 455                 460

Val Leu Thr Val Asn Pro Leu Val Val Asn Trp Arg Asn Asn Thr Val
465                 470                 475                 480

Ile Ser Arg Pro Gly Gln Ser Gln Cys Pro Arg Phe Asn Thr Cys Pro
                485                 490                 495

Glu Ile Cys Trp Glu Gly Val Tyr Asn Asp Ala Phe Leu Ile Asp Arg
            500                 505                 510

Ile Asn Trp Ile Ser Ala Gly Val Phe Leu Asp Ser Asn Gln Thr Ala
            515                 520                 525

Glu Asn Pro Val Phe Thr Val Phe Lys Asp Asn Glu Ile Leu Tyr Arg
            530                 535                 540

Ala Gln Leu Ala Ser Glu Asp Thr Asn Ala Gln Lys Thr Ile Thr Asn
545                 550                 555                 560
```

Cys Phe Leu Leu Lys Asn Lys Ile Trp Cys Ile Ser Leu Val Glu Ile
                565                 570                 575

Tyr Asp Thr Gly Asp Asn Val Ile Arg Pro Lys Leu Phe Ala Val Lys
        580                 585                 590

Ile Pro Glu Gln Cys Tyr Pro Tyr Asp Val Pro Asp Tyr Ala
        595                 600                 605

<210> SEQ ID NO 14
<211> LENGTH: 1821
<212> TYPE: DNA
<213> ORGANISM: Artificial Sequence
<220> FEATURE:
<223> OTHER INFORMATION: Variant nucleotide

<400> SEQUENCE: 14

| | | | | | |
|---|---|---|---|---|---|
| atgggaaaag | tgcggttcga | gaacaccaca | agcgacaagg | gcaagatccc | cagcaaagtg | 60 |
| atcaagagct | actacggcac | catggacatc | aagaagatca | acgagggcct | gctggacagc | 120 |
| aagatcctga | gcgccttcaa | caccgtgatc | gccctgctgg | gcagcatcgt | gatcattgtg | 180 |
| atgaacatca | tgatcatcca | gaactacacc | cggagcaccg | acaaccaggc | cgtgatcaag | 240 |
| gacgccctgc | agggaatcca | gcagcagatc | aagggcctgg | ccgacaagat | cggcaccgag | 300 |
| atcggcccca | agtgagcct | gatcgacacc | agcagcacca | tcaccatccc | cgccaacatc | 360 |
| ggcctgctgg | gatccaagat | cagccagagc | accgccagca | tcaacgagaa | cgtgaacgag | 420 |
| aagtgcaagt | tcaccctgcc | cccctgaag | atccacgagt | gcaacatcag | ctgccccaac | 480 |
| cccctgccct | tccgggagta | ccggcccag | accgagggcg | tgagcaacct | ggtgggcctg | 540 |
| cccaacaaca | tctgcctgca | gaaaaccagc | aaccagatcc | tgaagcccaa | gctgatctcc | 600 |
| tacaccctgc | ccgtggtggg | ccagagcggc | acctgcatca | ccgaccccct | gctggccatg | 660 |
| gacgagggct | acttcgccta | cagccacctg | agcggatcg | cagctgcag | ccggggagtg | 720 |
| agcaagcagc | ggatcatcgg | cgtgggcgaa | gtgctggacc | ggggcgacga | agtgcccagc | 780 |
| ctgttcatga | ccaacgtgtg | gacccccccc | aaccccaaca | ccgtgtacca | ctgcagcgcc | 840 |
| gtgtacaaca | acgagttcta | ctacgtgctg | tgcgccgtga | gcaccgtggg | cgaccccatc | 900 |
| ctgaacagca | cctactggag | cggcagcctg | atgatgaccc | ggctggccgt | gaagcctaag | 960 |
| agcaacggcg | aggctacaa | ccagcaccag | ctggccctgc | ggagcatcga | aagggccgg | 1020 |
| tacgacaaag | tgatgcccta | cggccccagc | ggcatcaagc | agggcgacac | cctgtacttc | 1080 |
| cccgccgtgg | gcttcctggt | gcggaccgag | ttcaagtaca | acgacagcaa | ctgccccatc | 1140 |
| accaagtgcc | agtacagcaa | gcccgagaac | tgccggctga | gcatgggcat | ccggcccaac | 1200 |
| agccactaca | tcctgcggag | cggcctgctg | aagtacaacc | tgagcgacgg | cgagaacccc | 1260 |
| aaagtggtgt | tcatcgagat | cagcgaccag | agactgagca | tcggcagccc | cagcaagatc | 1320 |
| tacgacagcc | tgggccagcc | cgtgttctac | caggccagct | tcagctggga | caccatgatc | 1380 |
| aagttcggcg | acgtgctgac | cgtgaacccc | tggtggtga | actggcggaa | caataccgtg | 1440 |
| atcagcagac | ccggccagag | ccagtgcccc | cggttcaaca | cctgccccga | gatctgctgg | 1500 |
| gagggcgtgt | acaacgacgc | cttcctgatc | gaccggatca | actggatcag | cgccggagtg | 1560 |
| ttcctggata | gcaaccagac | cgccgagaat | cccgtgttca | ccgtgtttaa | ggacaacgag | 1620 |
| atcctgtaca | gagcccagct | ggccagcgag | gacaccaacg | cccagaaaac | catcaccaac | 1680 |
| tgcttcctgc | tgaagaataa | gatctggtgc | atcagcctgg | tggagatcta | cgataccggc | 1740 |
| gacaacgtga | tcaggcccaa | gctgttcgcc | gtgaagatcc | ccgagcagtg | ctaccectac | 1800 | gacgtgcccg actacgcctg a                                                1821

<210> SEQ ID NO 15
<211> LENGTH: 601
<212> TYPE: PRT
<213> ORGANISM: Artificial Sequence
<220> FEATURE:
<223> OTHER INFORMATION: Variant peptide

<400> SEQUENCE: 15

```
Met Gly Asn Thr Thr Ser Asp Lys Gly Lys Ile Pro Ser Lys Val Ile
1               5                   10                  15

Lys Ser Tyr Tyr Gly Thr Met Asp Ile Lys Lys Ile Asn Glu Gly Leu
            20                  25                  30

Leu Asp Ser Lys Ile Leu Ser Ala Phe Asn Thr Val Ile Ala Leu Leu
        35                  40                  45

Gly Ser Ile Val Ile Ile Val Met Asn Ile Met Ile Ile Gln Asn Tyr
    50                  55                  60

Thr Arg Ser Thr Asp Asn Gln Ala Val Ile Lys Asp Ala Leu Gln Gly
65                  70                  75                  80

Ile Gln Gln Gln Ile Lys Gly Leu Ala Asp Lys Ile Gly Thr Glu Ile
                85                  90                  95

Gly Pro Lys Val Ser Leu Ile Asp Thr Ser Ser Thr Ile Thr Ile Pro
            100                 105                 110

Ala Asn Ile Gly Leu Leu Gly Ser Lys Ile Ser Gln Ser Thr Ala Ser
        115                 120                 125

Ile Asn Glu Asn Val Asn Glu Lys Cys Lys Phe Thr Leu Pro Pro Leu
    130                 135                 140

Lys Ile His Glu Cys Asn Ile Ser Cys Pro Asn Pro Leu Pro Phe Arg
145                 150                 155                 160

Glu Tyr Arg Pro Gln Thr Glu Gly Val Ser Asn Leu Val Gly Leu Pro
                165                 170                 175

Asn Asn Ile Cys Leu Gln Lys Thr Ser Asn Gln Ile Leu Lys Pro Lys
            180                 185                 190

Leu Ile Ser Tyr Thr Leu Pro Val Val Gly Gln Ser Gly Thr Cys Ile
        195                 200                 205

Thr Asp Pro Leu Leu Ala Met Asp Glu Gly Tyr Phe Ala Tyr Ser His
    210                 215                 220

Leu Glu Arg Ile Gly Ser Cys Ser Arg Gly Val Ser Lys Gln Arg Ile
225                 230                 235                 240

Ile Gly Val Gly Glu Val Leu Asp Arg Gly Asp Glu Val Pro Ser Leu
                245                 250                 255

Phe Met Thr Asn Val Trp Thr Pro Pro Asn Pro Asn Thr Val Tyr His
            260                 265                 270

Cys Ser Ala Val Tyr Asn Asn Glu Phe Tyr Tyr Val Leu Cys Ala Val
        275                 280                 285

Ser Thr Val Gly Asp Pro Ile Leu Asn Ser Thr Tyr Trp Ser Gly Ser
    290                 295                 300

Leu Met Met Thr Arg Leu Ala Val Lys Pro Lys Ser Asn Gly Gly Gly
305                 310                 315                 320

Tyr Asn Gln His Gln Leu Ala Leu Arg Ser Ile Glu Lys Gly Arg Tyr
                325                 330                 335

Asp Lys Val Met Pro Tyr Gly Pro Ser Gly Ile Lys Gln Gly Asp Thr
            340                 345                 350
```

| | | | | | | | | | | | |
|---|---|---|---|---|---|---|---|---|---|---|---|
|Leu|Tyr|Phe|Pro|Ala|Val|Gly|Phe|Leu|Val|Arg|Thr|Glu|Phe|Lys|Tyr|
| | |355| | | |360| | | |365| |

Asn Asp Ser Asn Cys Pro Ile Thr Lys Cys Gln Tyr Ser Lys Pro Glu
370 375 380

Asn Cys Arg Leu Ser Met Gly Ile Arg Pro Asn Ser His Tyr Ile Leu
385 390 395 400

Arg Ser Gly Leu Leu Lys Tyr Asn Leu Ser Asp Gly Glu Asn Pro Lys
405 410 415

Val Val Phe Ile Glu Ile Ser Asp Gln Arg Leu Ser Ile Gly Ser Pro
420 425 430

Ser Lys Ile Tyr Asp Ser Leu Gly Gln Pro Val Phe Tyr Gln Ala Ser
435 440 445

Phe Ser Trp Asp Thr Met Ile Lys Phe Gly Asp Val Leu Thr Val Asn
450 455 460

Pro Leu Val Val Asn Trp Arg Asn Asn Thr Val Ile Ser Arg Pro Gly
465 470 475 480

Gln Ser Gln Cys Pro Arg Phe Asn Thr Cys Pro Glu Ile Cys Trp Glu
485 490 495

Gly Val Tyr Asn Asp Ala Phe Leu Ile Asp Arg Ile Asn Trp Ile Ser
500 505 510

Ala Gly Val Phe Leu Asp Ser Asn Gln Thr Ala Glu Asn Pro Val Phe
515 520 525

Thr Val Phe Lys Asp Asn Glu Ile Leu Tyr Arg Ala Gln Leu Ala Ser
530 535 540

Glu Asp Thr Asn Ala Gln Lys Thr Ile Thr Asn Cys Phe Leu Leu Lys
545 550 555 560

Asn Lys Ile Trp Cys Ile Ser Leu Val Glu Ile Tyr Asp Thr Gly Asp
565 570 575

Asn Val Ile Arg Pro Lys Leu Phe Ala Val Lys Ile Pro Glu Gln Cys
580 585 590

Tyr Pro Tyr Asp Val Pro Asp Tyr Ala
595 600

<210> SEQ ID NO 16
<211> LENGTH: 1806
<212> TYPE: DNA
<213> ORGANISM: Artificial Sequence
<220> FEATURE:
<223> OTHER INFORMATION: Variant nucleotide

<400> SEQUENCE: 16

```
atgggaaaca ccacaagcga caagggcaag atccccagca aagtgatcaa gagctactac      60
ggcaccatgg acatcaagaa gatcaacgag ggcctgctgg acagcaagat cctgagcgcc     120
ttcaacaccg tgatcgccct gctgggcagc atcgtgatca ttgtgatgaa catcatgatc     180
atccagaact acacccggag caccgacaac caggccgtga tcaaggacgc cctgcaggga     240
atccagcagc agatcaaggg cctggccgac aagatcggca ccgagatcgg ccccaaagtg     300
agcctgatcg acaccagcag caccatcacc atccccgcca catcggcct gctgggatcc     360 aagatcagcc agagcaccgc cagcatcaac gagaacgtga cgagaagtg caagttcacc     420 ctgccccccc tgaagatcca cgagtgcaac atcagctgcc ccaaccccct gcccttccgg     480
gagtaccggc cccagaccga gggcgtgagc aacctggtgg gcctgccaa caacatctgc     540 ctgcagaaaa ccagcaacca gatcctgaag cccaagctga tctcctacac cctgcccgtg     600
gtgggccaga gcggcaccg catcaccgac ccctgctgg ccatggacga gggctacttc     660
```

-continued

```
gcctacagcc acctggagcg atcggcagc tgcagccggg gagtgagcaa gcagcggatc    720
atcggcgtgg gcgaagtgct ggaccggggc gacgaagtgc ccagcctgtt catgaccaac    780
gtgtggaccc cccccaaccc caacaccgtg taccactgca cgccgtgta caacaacgag     840
ttctactacg tgctgtgcgc cgtgagcacc gtgggcgacc ccatcctgaa cagcacctac    900
tggagcggca gcctgatgat gacccggctg ccgtgaagc ctaagagcaa cggcggaggc     960
tacaaccagc accagctggc cctgcgcagc atcgagaagg gccggtacga caaagtgatg   1020
ccctacggcc cagcggcat caagcagggc gacaccctgt acttccccgc cgtgggcttc    1080
ctggtgcgga ccgagttcaa gtacaacgac agcaactgcc ccatcaccaa gtgccagtac   1140
agcaagcccg agaactgccg gctgagcatg ggcatccggc ccaacagcca ctacatcctg   1200
cggagcggcc tgctgaagta caacctgagc gacggcgaga accccaaagt ggtgttcatc   1260
gagatcagcg accagagact gagcatcggc agccccagca agatctacga cagcctgggc   1320
cagcccgtgt ctaccaggc cagcttcagc tgggacacca tgatcaagtt cggcgacgtg    1380
ctgaccgtga acccctggt ggtgaactgg cggaacaata ccgtgatcag cagacccggc   1440
cagagccagt gccccggtt caacacctgc cccgagatct gctgggaggg cgtgtacaac   1500
gacgccttcc tgatcgaccg gatcaactgg atcagcgccg gagtgttcct ggatagcaac   1560
cagaccgccg agaatcccgt gttcaccgtg tttaaggaca acgagatcct gtacagagcc   1620
cagctggcca gcgaggacac caacgcccag aaaaccatca ccaactgctt cctgctgaag   1680
aataagatct ggtgcatcag cctggtggag atctacgata ccggcgacaa cgtgatcagg   1740
cccaagctgt tcgccgtgaa gatccccgag cagtgctacc cctacgacgt gcccgactac   1800
gcctga                                                              1806
```

<210> SEQ ID NO 17
<211> LENGTH: 596
<212> TYPE: PRT
<213> ORGANISM: Artificial Sequence
<220> FEATURE:
<223> OTHER INFORMATION: Variant peptide

<400> SEQUENCE: 17

```
Met Gly Lys Gly Lys Ile Pro Ser Lys Val Ile Lys Ser Tyr Tyr Gly
1               5                   10                  15

Thr Met Asp Ile Lys Lys Ile Asn Glu Gly Leu Leu Asp Ser Lys Ile
            20                  25                  30

Leu Ser Ala Phe Asn Thr Val Ile Ala Leu Leu Gly Ser Ile Val Ile
        35                  40                  45

Ile Val Met Asn Ile Met Ile Ile Gln Asn Tyr Thr Arg Ser Thr Asp
    50                  55                  60

Asn Gln Ala Val Ile Lys Asp Ala Leu Gln Gly Ile Gln Gln Gln Ile
65                  70                  75                  80

Lys Gly Leu Ala Asp Lys Ile Gly Thr Glu Ile Gly Pro Lys Val Ser
                85                  90                  95

Leu Ile Asp Thr Ser Ser Thr Ile Thr Ile Pro Ala Asn Ile Gly Leu
            100                 105                 110

Leu Gly Ser Lys Ile Ser Gln Ser Thr Ala Ser Ile Asn Glu Asn Val
        115                 120                 125

Asn Glu Lys Cys Lys Phe Thr Leu Pro Pro Leu Lys Ile His Glu Cys
    130                 135                 140
```

-continued

```
Asn Ile Ser Cys Pro Asn Pro Leu Pro Phe Arg Glu Tyr Arg Pro Gln
145                 150                 155                 160

Thr Glu Gly Val Ser Asn Leu Val Gly Leu Pro Asn Asn Ile Cys Leu
            165                 170                 175

Gln Lys Thr Ser Asn Gln Ile Leu Lys Pro Lys Leu Ile Ser Tyr Thr
        180                 185                 190

Leu Pro Val Val Gly Gln Ser Gly Thr Cys Ile Thr Asp Pro Leu Leu
    195                 200                 205

Ala Met Asp Glu Gly Tyr Phe Ala Tyr Ser His Leu Glu Arg Ile Gly
    210                 215                 220

Ser Cys Ser Arg Gly Val Ser Lys Gln Arg Ile Ile Gly Val Gly Glu
225                 230                 235                 240

Val Leu Asp Arg Gly Asp Glu Val Pro Ser Leu Phe Met Thr Asn Val
            245                 250                 255

Trp Thr Pro Pro Asn Pro Asn Thr Val Tyr His Cys Ser Ala Val Tyr
            260                 265                 270

Asn Asn Glu Phe Tyr Tyr Val Leu Cys Ala Val Ser Thr Val Gly Asp
        275                 280                 285

Pro Ile Leu Asn Ser Thr Tyr Trp Ser Gly Ser Leu Met Met Thr Arg
    290                 295                 300

Leu Ala Val Lys Pro Lys Ser Asn Gly Gly Tyr Asn Gln His Gln
305                 310                 315                 320

Leu Ala Leu Arg Ser Ile Glu Lys Gly Arg Tyr Asp Lys Val Met Pro
            325                 330                 335

Tyr Gly Pro Ser Gly Ile Lys Gln Gly Asp Thr Leu Tyr Phe Pro Ala
            340                 345                 350

Val Gly Phe Leu Val Arg Thr Glu Phe Lys Tyr Asn Asp Ser Asn Cys
        355                 360                 365

Pro Ile Thr Lys Cys Gln Tyr Ser Lys Pro Glu Asn Cys Arg Leu Ser
    370                 375                 380

Met Gly Ile Arg Pro Asn Ser His Tyr Ile Leu Arg Ser Gly Leu Leu
385                 390                 395                 400

Lys Tyr Asn Leu Ser Asp Gly Glu Asn Pro Lys Val Val Phe Ile Glu
            405                 410                 415

Ile Ser Asp Gln Arg Leu Ser Ile Gly Ser Pro Ser Lys Ile Tyr Asp
            420                 425                 430

Ser Leu Gly Gln Pro Val Phe Tyr Gln Ala Ser Phe Ser Trp Asp Thr
        435                 440                 445

Met Ile Lys Phe Gly Asp Val Leu Thr Val Asn Pro Leu Val Val Asn
    450                 455                 460

Trp Arg Asn Asn Thr Val Ile Ser Arg Pro Gly Gln Ser Gln Cys Pro
465                 470                 475                 480

Arg Phe Asn Thr Cys Pro Glu Ile Cys Trp Glu Gly Val Tyr Asn Asp
            485                 490                 495

Ala Phe Leu Ile Asp Arg Ile Asn Trp Ile Ser Ala Gly Val Phe Leu
            500                 505                 510

Asp Ser Asn Gln Thr Ala Glu Asn Pro Val Phe Thr Val Phe Lys Asp
        515                 520                 525

Asn Glu Ile Leu Tyr Arg Ala Gln Leu Ala Ser Glu Asp Thr Asn Ala
    530                 535                 540

Gln Lys Thr Ile Thr Asn Cys Phe Leu Leu Lys Asn Lys Ile Trp Cys
545                 550                 555                 560
```

Ile Ser Leu Val Glu Ile Tyr Asp Thr Gly Asp Asn Val Ile Arg Pro
                565                 570                 575

Lys Leu Phe Ala Val Lys Ile Pro Glu Gln Cys Tyr Pro Tyr Asp Val
            580                 585                 590

Pro Asp Tyr Ala
        595

<210> SEQ ID NO 18
<211> LENGTH: 1791
<212> TYPE: DNA
<213> ORGANISM: Artificial Sequence
<220> FEATURE:
<223> OTHER INFORMATION: Variant nucleotide

<400> SEQUENCE: 18

| | | | | | |
|---|---|---|---|---|---|
| atgggaaagg | gcaagatccc | cagcaaagtg | atcaagagct | actacggcac | catggacatc | 60 |
| aagaagatca | acgagggcct | gctggacagc | aagatcctga | gcgccttcaa | caccgtgatc | 120 |
| gccctgctgg | gcagcatcgt | gatcattgtg | atgaacatca | tgatcatcca | gaactacacc | 180 |
| cggagcaccg | acaaccaggc | cgtgatcaag | gacgccctgc | agggaatcca | gcagcagatc | 240 |
| aagggcctgg | ccgacaagat | cggcaccgag | atcggcccca | agtgagcct | gatcgacacc | 300 |
| agcagcacca | tcaccatccc | cgccaacatc | ggcctgctgg | atccaagat | cagccagagc | 360 |
| accgccagca | tcaacgagaa | cgtgaacgag | aagtgcaagt | tcaccctgcc | ccccctgaag | 420 |
| atccacgagt | gcaacatcag | ctgccccaac | ccctgccct | tccgggagta | ccggccccag | 480 |
| accgagggcg | tgagcaacct | ggtgggcctg | cccaacaaca | tctgcctgca | gaaaaccagc | 540 |
| aaccagatcc | tgaagcccaa | gctgatctcc | tacaccctgc | ccgtggtggg | ccagagcggc | 600 |
| acctgcatca | ccgaccccct | gctggccatg | gacgagggct | acttcgccta | cagccacctg | 660 |
| gagcggatcg | gcagctgcag | ccggggagtg | agcaagcagc | ggatcatcgg | cgtgggcgaa | 720 |
| gtgctggacc | ggggcgacga | agtgcccagc | ctgttcatga | ccaacgtgtg | daccccccc | 780 |
| aaccccaaca | ccgtgtacca | ctgcagcgcc | gtgtacaaca | acgagttcta | ctacgtgctg | 840 |
| tgcgccgtga | gcaccgtggg | cgaccccatc | ctgaacagca | cctactggag | cggcagcctg | 900 |
| atgatgaccc | ggctggccgt | gaagcctaag | agcaacggcg | gaggctacaa | ccagcaccag | 960 |
| ctggccctgc | ggagcatcga | gaagggccgg | tacgacaaag | tgatgcccta | cggccccagc | 1020 |
| ggcatcaagc | agggcgacac | cctgtacttc | cccgccgtgg | gcttcctggt | gcggaccgag | 1080 |
| ttcaagtaca | cgacagcaa | ctgccccatc | accaagtgcc | agtacagcaa | gcccgagaac | 1140 |
| tgccggctga | gcatgggcat | ccggcccaac | agccactaca | tcctgcggag | cggcctgctg | 1200 |
| aagtacaacc | tgagcgacgg | cgagaacccc | aaagtggtgt | tcatcgagat | cagcgaccag | 1260 |
| agactgagca | tcggcagccc | cagcaagatc | tacgacagcc | tgggccagcc | cgtgttctac | 1320 |
| caggccagct | tcagctggga | caccatgatc | aagttcggcg | acgtgctgac | cgtgaacccc | 1380 |
| ctggtggtga | actggcggaa | caataccgtg | atcagcagac | ccggcagag | ccagtgcccc | 1440 |
| cggttcaaca | cctgccccga | gatctgctgg | gagggcgtgt | acaacgacgc | cttcctgatc | 1500 |
| gaccggatca | actggatcag | cgccggagtg | ttcctggata | gcaaccagac | cgccgagaat | 1560 |
| cccgtgttca | ccgtgtttaa | ggacaacgag | atcctgtaca | gagcccagct | ggccagcgag | 1620 |
| gacaccaacg | cccagaaaac | catcaccaac | tgcttcctgc | tgaagaataa | gatctggtgc | 1680 |
| atcagcctgg | tggagatcta | cgataccggc | gacaacgtga | tcaggcccaa | gctgttcgcc | 1740 |
| gtgaagatcc | ccgagcagtg | ctacccctac | gacgtgcccg | actacgcctg | a | 1791 |

```
<210> SEQ ID NO 19
<211> LENGTH: 591
<212> TYPE: PRT
<213> ORGANISM: Artificial Sequence
<220> FEATURE:
<223> OTHER INFORMATION: Variant peptide

<400> SEQUENCE: 19

Met Gly Ser Lys Val Ile Lys Ser Tyr Tyr Gly Thr Met Asp Ile Lys
1               5                   10                  15

Lys Ile Asn Glu Gly Leu Leu Asp Ser Lys Ile Leu Ser Ala Phe Asn
                20                  25                  30

Thr Val Ile Ala Leu Leu Gly Ser Ile Val Ile Val Met Asn Ile
            35                  40                  45

Met Ile Ile Gln Asn Tyr Thr Arg Ser Thr Asp Asn Gln Ala Val Ile
    50                  55                  60

Lys Asp Ala Leu Gln Gly Ile Gln Gln Ile Lys Gly Leu Ala Asp
65              70                  75                  80

Lys Ile Gly Thr Glu Ile Gly Pro Lys Val Ser Leu Ile Asp Thr Ser
                85                  90                  95

Ser Thr Ile Thr Ile Pro Ala Asn Ile Gly Leu Leu Gly Ser Lys Ile
            100                 105                 110

Ser Gln Ser Thr Ala Ser Ile Asn Glu Asn Val Asn Glu Lys Cys Lys
        115                 120                 125

Phe Thr Leu Pro Pro Leu Lys Ile His Glu Cys Asn Ile Ser Cys Pro
130                 135                 140

Asn Pro Leu Pro Phe Arg Glu Tyr Arg Pro Gln Thr Glu Gly Val Ser
145                 150                 155                 160

Asn Leu Val Gly Leu Pro Asn Asn Ile Cys Leu Gln Lys Thr Ser Asn
                165                 170                 175

Gln Ile Leu Lys Pro Lys Leu Ile Ser Tyr Thr Leu Pro Val Val Gly
            180                 185                 190

Gln Ser Gly Thr Cys Ile Thr Asp Pro Leu Leu Ala Met Asp Glu Gly
        195                 200                 205

Tyr Phe Ala Tyr Ser His Leu Glu Arg Ile Gly Ser Cys Ser Arg Gly
210                 215                 220

Val Ser Lys Gln Arg Ile Ile Gly Val Gly Glu Val Leu Asp Arg Gly
225                 230                 235                 240

Asp Glu Val Pro Ser Leu Phe Met Thr Asn Val Trp Thr Pro Pro Asn
                245                 250                 255

Pro Asn Thr Val Tyr His Cys Ser Ala Val Tyr Asn Asn Glu Phe Tyr
            260                 265                 270

Tyr Val Leu Cys Ala Val Ser Thr Val Gly Asp Pro Ile Leu Asn Ser
        275                 280                 285

Thr Tyr Trp Ser Gly Ser Leu Met Met Thr Arg Leu Ala Val Lys Pro
290                 295                 300

Lys Ser Asn Gly Gly Gly Tyr Asn Gln His Gln Leu Ala Leu Arg Ser
305                 310                 315                 320

Ile Glu Lys Gly Arg Tyr Asp Lys Val Met Pro Tyr Gly Pro Ser Gly
                325                 330                 335

Ile Lys Gln Gly Asp Thr Leu Tyr Phe Pro Ala Val Gly Phe Leu Val
            340                 345                 350

Arg Thr Glu Phe Lys Tyr Asn Asp Ser Asn Cys Pro Ile Thr Lys Cys
        355                 360                 365
```

Gln Tyr Ser Lys Pro Glu Asn Cys Arg Leu Ser Met Gly Ile Arg Pro
    370                 375                 380

Asn Ser His Tyr Ile Leu Arg Ser Gly Leu Leu Lys Tyr Asn Leu Ser
385                 390                 395                 400

Asp Gly Glu Asn Pro Lys Val Val Phe Ile Glu Ile Ser Asp Gln Arg
                405                 410                 415

Leu Ser Ile Gly Ser Pro Ser Lys Ile Tyr Asp Ser Leu Gly Gln Pro
            420                 425                 430

Val Phe Tyr Gln Ala Ser Phe Ser Trp Asp Thr Met Ile Lys Phe Gly
        435                 440                 445

Asp Val Leu Thr Val Asn Pro Leu Val Val Asn Trp Arg Asn Asn Thr
450                 455                 460

Val Ile Ser Arg Pro Gly Gln Ser Gln Cys Pro Arg Phe Asn Thr Cys
465                 470                 475                 480

Pro Glu Ile Cys Trp Glu Gly Val Tyr Asn Asp Ala Phe Leu Ile Asp
                485                 490                 495

Arg Ile Asn Trp Ile Ser Ala Gly Val Phe Leu Asp Ser Asn Gln Thr
            500                 505                 510

Ala Glu Asn Pro Val Phe Thr Val Phe Lys Asp Asn Glu Ile Leu Tyr
        515                 520                 525

Arg Ala Gln Leu Ala Ser Glu Asp Thr Asn Ala Gln Lys Thr Ile Thr
530                 535                 540

Asn Cys Phe Leu Leu Lys Asn Lys Ile Trp Cys Ile Ser Leu Val Glu
545                 550                 555                 560

Ile Tyr Asp Thr Gly Asp Asn Val Ile Arg Pro Lys Leu Phe Ala Val
                565                 570                 575

Lys Ile Pro Glu Gln Cys Tyr Pro Tyr Asp Val Pro Asp Tyr Ala
            580                 585                 590

<210> SEQ ID NO 20
<211> LENGTH: 1776
<212> TYPE: DNA
<213> ORGANISM: Artificial Sequence
<220> FEATURE:
<223> OTHER INFORMATION: Variant nucleotide

<400> SEQUENCE: 20
atgggaagca aagtgatcaa gagctactac ggcaccatgg acatcaagaa gatcaacgag      60
ggcctgctgg acagcaagat cctgagcgcc ttcaacaccg tgatcgccct gctgggcagc     120
atcgtgatca ttgtgatgaa catcatgatc atccagaact acaccggag caccgacaac      180 caggccgtga tcaaggacgc cctgcaggga atccagcagc agatcaaggg cctggccgac     240
aagatcggca ccgagatcgg ccccaaagtg agcctgatcg acaccagcag caccatcacc     300
atccccgcca catcggcct gctgggatcc aagatcagcc agagcaccgc cagcatcaac      360
gagaacgtga cgagaagtg caagttcacc ctgcccccc tgaagatcca cgagtgcaac       420
atcagctgcc ccaaccccct gcccttccgg gagtaccggc cccagaccga gggcgtgagc     480
aacctggtgg gcctgcccaa caacatctgc ctgcagaaaa ccagcaacca gatcctgaag     540
cccaagctga tctcctacac cctgcccgtg gtgggccaga gcggcaccctg catcaccgac   600 cccctgctgg ccatggacga gggctacttc gcctacagcc acctggagcg gatcggcagc     660
tgcagccggg gagtgagcaa gcagcggatc atcggcgtgg gcgaagtgct ggaccggggc     720
gacgaagtgc ccagcctgtt catgaccaac gtgtggaccc cccccaaccc caacaccgtg     780
taccactgca gcgccgtgta caacaacgag ttctactacg tgctgtgcgc cgtgagcacc     840

```
gtgggcgacc ccatcctgaa cagcacctac tggagcggca gcctgatgat gacccggctg    900
gccgtgaagc ctaagagcaa cggcggaggc tacaaccagc accagctggc cctgcggagc    960
atcgagaagg ccggtacga caaagtgatg ccctacggcc ccagcggcat caagcagggc   1020
gacaccctgt acttccccgc cgtgggcttc ctggtgcgga ccgagttcaa gtacaacgac   1080
agcaactgcc ccatcaccaa gtgccagtac agcaagcccg agaactgccg gctgagcatg   1140
ggcatccggc ccaacagcca ctacatcctg cggagcggcc tgctgaagta caacctgagc   1200
gacggcgaga accccaaagt ggtgttcatc gagatcagcg accagagact gagcatcggc   1260
agccccagca agatctacga cagcctgggc cagcccgtgt cctaccaggc cagcttcagc   1320
tgggacacca tgatcaagtt cggcgacgtg ctgaccgtga accccctggt ggtgaactgg   1380
cggaacaata ccgtgatcag cagacccggc cagagccagt gccccggtt caacacctgc    1440
cccgagatct gctgggaggg cgtgtacaac gacgccttcc tgatcgaccg gatcaactgg   1500
atcagcgccg gagtgttcct ggatagcaac cagaccgccg agaatcccgt gttcaccgtg   1560
tttaaggaca acgagatcct gtacagagcc cagctggcca gcgaggacac caacgcccag   1620
aaaaccatca ccaactgctt cctgctgaag aataagatct ggtgcatcag cctggtggag   1680
atctacgata ccggcgacaa cgtgatcagg cccaagctgt cgccgtgaa gatccccgag     1740
cagtgctacc cctacgacgt gcccgactac gcctga                              1776
```

<210> SEQ ID NO 21
<211> LENGTH: 586
<212> TYPE: PRT
<213> ORGANISM: Artificial Sequence
<220> FEATURE:
<223> OTHER INFORMATION: Variant peptide

<400> SEQUENCE: 21

```
Met Gly Ser Tyr Tyr Gly Thr Met Asp Ile Lys Lys Ile Asn Glu Gly
1               5                   10                  15

Leu Leu Asp Ser Lys Ile Leu Ser Ala Phe Asn Thr Val Ile Ala Leu
                20                  25                  30

Leu Gly Ser Ile Val Ile Val Met Asn Ile Met Ile Ile Gln Asn
            35                  40                  45

Tyr Thr Arg Ser Thr Asp Asn Gln Ala Val Ile Lys Asp Ala Leu Gln
    50                  55                  60

Gly Ile Gln Gln Gln Ile Lys Gly Leu Ala Asp Lys Ile Gly Thr Glu
65                  70                  75                  80

Ile Gly Pro Lys Val Ser Leu Ile Asp Thr Ser Ser Thr Ile Thr Ile
                85                  90                  95

Pro Ala Asn Ile Gly Leu Leu Gly Ser Lys Ile Ser Gln Ser Thr Ala
            100                 105                 110

Ser Ile Asn Glu Asn Val Asn Glu Lys Cys Lys Phe Thr Leu Pro Pro
        115                 120                 125

Leu Lys Ile His Glu Cys Asn Ile Ser Cys Pro Asn Pro Leu Pro Phe
    130                 135                 140

Arg Glu Tyr Arg Pro Gln Thr Glu Gly Val Ser Asn Leu Val Gly Leu
145                 150                 155                 160

Pro Asn Asn Ile Cys Leu Gln Lys Thr Ser Asn Gln Ile Leu Lys Pro
                165                 170                 175

Lys Leu Ile Ser Tyr Thr Leu Pro Val Val Gly Gln Ser Gly Thr Cys
            180                 185                 190
```

Ile Thr Asp Pro Leu Leu Ala Met Asp Glu Gly Tyr Phe Ala Tyr Ser
     195                 200                 205

His Leu Glu Arg Ile Gly Ser Cys Ser Arg Gly Val Ser Lys Gln Arg
    210                 215                 220

Ile Ile Gly Val Gly Glu Val Leu Asp Arg Gly Asp Glu Val Pro Ser
225                 230                 235                 240

Leu Phe Met Thr Asn Val Trp Thr Pro Pro Asn Pro Asn Thr Val Tyr
                245                 250                 255

His Cys Ser Ala Val Tyr Asn Asn Glu Phe Tyr Val Leu Cys Ala
                260                 265                 270

Val Ser Thr Val Gly Asp Pro Ile Leu Asn Ser Thr Tyr Trp Ser Gly
    275                 280                 285

Ser Leu Met Met Thr Arg Leu Ala Val Lys Pro Lys Ser Asn Gly Gly
    290                 295                 300

Gly Tyr Asn Gln His Gln Leu Ala Leu Arg Ser Ile Glu Lys Gly Arg
305                 310                 315                 320

Tyr Asp Lys Val Met Pro Tyr Gly Pro Ser Gly Ile Lys Gln Gly Asp
                325                 330                 335

Thr Leu Tyr Phe Pro Ala Val Gly Phe Leu Val Arg Thr Glu Phe Lys
                340                 345                 350

Tyr Asn Asp Ser Asn Cys Pro Ile Thr Lys Cys Gln Tyr Ser Lys Pro
                355                 360                 365

Glu Asn Cys Arg Leu Ser Met Gly Ile Arg Pro Asn Ser His Tyr Ile
                370                 375                 380

Leu Arg Ser Gly Leu Leu Lys Tyr Asn Leu Ser Asp Gly Glu Asn Pro
385                 390                 395                 400

Lys Val Val Phe Ile Glu Ile Ser Asp Gln Arg Leu Ser Ile Gly Ser
                405                 410                 415

Pro Ser Lys Ile Tyr Asp Ser Leu Gly Gln Pro Val Phe Tyr Gln Ala
                420                 425                 430

Ser Phe Ser Trp Asp Thr Met Ile Lys Phe Gly Asp Val Leu Thr Val
                435                 440                 445

Asn Pro Leu Val Val Asn Trp Arg Asn Asn Thr Val Ile Ser Arg Pro
450                 455                 460

Gly Gln Ser Gln Cys Pro Arg Phe Asn Thr Cys Pro Glu Ile Cys Trp
465                 470                 475                 480

Glu Gly Val Tyr Asn Asp Ala Phe Leu Ile Asp Arg Ile Asn Trp Ile
                485                 490                 495

Ser Ala Gly Val Phe Leu Asp Ser Asn Gln Thr Ala Glu Asn Pro Val
                500                 505                 510

Phe Thr Val Phe Lys Asp Asn Glu Ile Leu Tyr Arg Ala Gln Leu Ala
                515                 520                 525

Ser Glu Asp Thr Asn Ala Gln Lys Thr Ile Thr Asn Cys Phe Leu Leu
    530                 535                 540

Lys Asn Lys Ile Trp Cys Ile Ser Leu Val Glu Ile Tyr Asp Thr Gly
545                 550                 555                 560

Asp Asn Val Ile Arg Pro Lys Leu Phe Ala Val Lys Ile Pro Glu Gln
                565                 570                 575

Cys Tyr Pro Tyr Asp Val Pro Asp Tyr Ala
                580                 585

<210> SEQ ID NO 22
<211> LENGTH: 1761
<212> TYPE: DNA

<210> ORGANISM: Artificial Sequence
<220> FEATURE:
<223> OTHER INFORMATION: Variant nucleotide

<400> SEQUENCE: 22

```
atgggaagct actacggcac catggacatc aagaagatca acgagggcct gctggacagc     60
aagatcctga gcgccttcaa caccgtgatc gccctgctgg gcagcatcgt gatcattgtg    120
atgaacatca tgatcatcca gaactacacc cggagcaccg acaaccaggc cgtgatcaag    180
gacgccctgc agggaatcca gcagcagatc aagggcctgg ccgacaagat cggcaccgag    240
atcggcccca agtgagcct gatcgacacc agcagcacca tcaccatccc cgccaacatc     300
ggcctgctgg gatccaagat cagccagagc accgccagca tcaacgagaa cgtgaacgag    360
aagtgcaagt tcaccctgcc ccccctgaag atccacgagt gcaacatcag ctgcccaac     420
ccctgccct tccgggagta ccggccccag accgagggcg tgagcaacct ggtgggcctg     480
cccaacaaca tctgcctgca gaaaaccagc aaccagatcc tgaagcccaa gctgatctcc    540
tacaccctgc ccgtggtggg ccagagcggc acctgcatca ccgacccct gctggccatg     600
gacgagggct acttcgccta cagccacctg gagcggatcg gcagctgcag ccggggagtg    660
agcaagcagc ggatcatcgg cgtgggcgaa gtgctggacc ggggcgacga agtgccagc    720
ctgttcatga ccaacgtgtg accccccccc aaccccaaca ccgtgtacca ctgcagcgcc    780
gtgtacaaca acgagttcta ctacgtgctg tgcgccgtga gcaccgtggg cgaccccatc    840
ctgaacagca cctactggag cggcagcctg atgatgaccc ggctggccgt gaagcctaag    900
agcaacggcg aggctacaa ccagcaccag ctggccctgc ggagcatcga aagggccgg     960
tacgacaaag tgatgcccta cggccccagc ggcatcaagc agggcgacac cctgtacttc   1020
cccgccgtgg gcttcctggt gcggaccgag ttcaagtaca cgacagcaa ctgccccatc   1080
accaagtgcc agtacagcaa gcccgagaac tgccggctga gcatgggcat ccggcccaac   1140
agccactaca tcctgcggag cggcctgctg aagtacaacc tgagcgacgg cgagaacccc   1200
aaagtggtgt tcatcgagat cagcgaccag agactgagca tcggcagccc cagcaagatc   1260
tacgacagcc tgggccagcc cgtgttctac caggccagct tcagctggga ccaccatgatc  1320
aagttcggcg acgtgctgac cgtgaacccc ctggtggtga actggcggaa caataccgtg   1380
atcagcagac ccgccagag ccagtgcccc cggttcaaca cctgccccga gatctgctgg    1440
gagggcgtgt acaacgacgc cttcctgatc gaccggatca actggatcag cgccggagtg   1500
ttcctggata gcaaccagac cgccgagaat cccgtgttca ccgtgtttaa ggacaacgag   1560
atcctgtaca gagcccagct ggccagcgag gacaccaacg cccagaaaac catcaccaac   1620
tgcttcctgc tgaagaataa gatctggtgc atcagcctgg tggagatcta cgataccggc   1680
gacaacgtga tcaggcccaa gctgttcgcc gtgaagatcc ccgagcagtg ctacccctac   1740
gacgtgcccg actacgcctg a                                              1761
```

<210> SEQ ID NO 23
<211> LENGTH: 581
<212> TYPE: PRT
<213> ORGANISM: Artificial Sequence
<220> FEATURE:
<223> OTHER INFORMATION: Variant peptide

<400> SEQUENCE: 23

```
Gly Thr Met Asp Ile Lys Lys Ile Asn Glu Gly Leu Leu Asp Ser Lys
1               5                   10                  15
```

```
Ile Leu Ser Ala Phe Asn Thr Val Ile Ala Leu Leu Gly Ser Ile Val
             20                  25                  30

Ile Ile Val Met Asn Ile Met Ile Ile Gln Asn Tyr Thr Arg Ser Thr
         35                  40                  45

Asp Asn Gln Ala Val Ile Lys Asp Ala Leu Gln Gly Ile Gln Gln Gln
     50                  55                  60

Ile Lys Gly Leu Ala Asp Lys Ile Gly Thr Glu Ile Gly Pro Lys Val
 65                  70                  75                  80

Ser Leu Ile Asp Thr Ser Ser Thr Ile Thr Ile Pro Ala Asn Ile Gly
                 85                  90                  95

Leu Leu Gly Ser Lys Ile Ser Gln Ser Thr Ala Ser Ile Asn Glu Asn
            100                 105                 110

Val Asn Glu Lys Cys Lys Phe Thr Leu Pro Pro Leu Lys Ile His Glu
        115                 120                 125

Cys Asn Ile Ser Cys Pro Asn Pro Leu Pro Phe Arg Glu Tyr Arg Pro
    130                 135                 140

Gln Thr Glu Gly Val Ser Asn Leu Val Gly Leu Pro Asn Asn Ile Cys
145                 150                 155                 160

Leu Gln Lys Thr Ser Asn Gln Ile Leu Lys Pro Lys Leu Ile Ser Tyr
                165                 170                 175

Thr Leu Pro Val Val Gly Gln Ser Gly Thr Cys Ile Thr Asp Pro Leu
            180                 185                 190

Leu Ala Met Asp Glu Gly Tyr Phe Ala Tyr Ser His Leu Glu Arg Ile
        195                 200                 205

Gly Ser Cys Ser Arg Gly Val Ser Lys Gln Arg Ile Ile Gly Val Gly
    210                 215                 220

Glu Val Leu Asp Arg Gly Asp Glu Val Pro Ser Leu Phe Met Thr Asn
225                 230                 235                 240

Val Trp Thr Pro Pro Asn Pro Asn Thr Val Tyr His Cys Ser Ala Val
                245                 250                 255

Tyr Asn Asn Glu Phe Tyr Tyr Val Leu Cys Ala Val Ser Thr Val Gly
            260                 265                 270

Asp Pro Ile Leu Asn Ser Thr Tyr Trp Ser Gly Ser Leu Met Met Thr
        275                 280                 285

Arg Leu Ala Val Lys Pro Lys Ser Asn Gly Gly Gly Tyr Asn Gln His
    290                 295                 300

Gln Leu Ala Leu Arg Ser Ile Glu Lys Gly Arg Tyr Asp Lys Val Met
305                 310                 315                 320

Pro Tyr Gly Pro Ser Gly Ile Lys Gln Gly Asp Thr Leu Tyr Phe Pro
                325                 330                 335

Ala Val Gly Phe Leu Val Arg Thr Glu Phe Lys Tyr Asn Asp Ser Asn
            340                 345                 350

Cys Pro Ile Thr Lys Cys Gln Tyr Ser Lys Pro Glu Asn Cys Arg Leu
        355                 360                 365

Ser Met Gly Ile Arg Pro Asn Ser His Tyr Ile Leu Arg Ser Gly Leu
    370                 375                 380

Leu Lys Tyr Asn Leu Ser Asp Gly Glu Asn Pro Lys Val Val Phe Ile
385                 390                 395                 400

Glu Ile Ser Asp Gln Arg Leu Ser Ile Gly Ser Pro Ser Lys Ile Tyr
                405                 410                 415

Asp Ser Leu Gly Gln Pro Val Phe Tyr Gln Ala Ser Phe Ser Trp Asp
            420                 425                 430
```

```
Thr Met Ile Lys Phe Gly Asp Val Leu Thr Val Asn Pro Leu Val Val
            435                 440                 445
Asn Trp Arg Asn Asn Thr Val Ile Ser Arg Pro Gly Gln Ser Gln Cys
450                 455                 460
Pro Arg Phe Asn Thr Cys Pro Glu Ile Cys Trp Glu Gly Val Tyr Asn
465                 470                 475                 480
Asp Ala Phe Leu Ile Asp Arg Ile Asn Trp Ile Ser Ala Gly Val Phe
                485                 490                 495
Leu Asp Ser Asn Gln Thr Ala Glu Asn Pro Val Phe Thr Val Phe Lys
                500                 505                 510
Asp Asn Glu Ile Leu Tyr Arg Ala Gln Leu Ala Ser Glu Asp Thr Asn
            515                 520                 525
Ala Gln Lys Thr Ile Thr Asn Cys Phe Leu Leu Lys Asn Lys Ile Trp
            530                 535                 540
Cys Ile Ser Leu Val Glu Ile Tyr Asp Thr Gly Asp Asn Val Ile Arg
545                 550                 555                 560
Pro Lys Leu Phe Ala Val Lys Ile Pro Glu Gln Cys Tyr Pro Tyr Asp
                565                 570                 575
Val Pro Asp Tyr Ala
            580

<210> SEQ ID NO 24
<211> LENGTH: 1746
<212> TYPE: DNA
<213> ORGANISM: Artificial Sequence
<220> FEATURE:
<223> OTHER INFORMATION: Variant nucleotide

<400> SEQUENCE: 24
ggcaccatgg acatcaagaa gatcaacgag ggcctgctgg acagcaagat cctgagcgcc      60
ttcaacaccg tgatcgccct gctgggcagc atcgtgatca ttgtgatgaa catcatgatc     120
atccagaact acacccggag caccgacaac caggccgtga tcaaggacgc cctgcaggga     180
atccagcagc agatcaaggg cctggccgac aagatcggca ccgagatcgg ccccaaagtg     240
agcctgatcg acaccagcag caccatcacc atccccgcca catcggcct gctgggatcc     300
aagatcagcc agagcaccgc cagcatcaac gagaacgtga cgagaagtg caagttcacc     360
ctgcccccc tgaagatcca cgagtgcaac atcagctgcc ccaacccct gcccttccgg      420
gagtaccggc cccagaccga gggcgtgagc aacctggtgg gcctgcccaa caacatctgc    480
ctgcagaaaa ccagcaacca gatcctgaag cccaagctga tctcctacac cctgcccgtg    540
gtgggccaga gcggcaccctg catcaccgac cccctgctgg ccatggacga gggctacttc    600
gcctacagcc acctggagcg gatcggcagc tgcagccggg gagtgagcaa gcagcggatc    660
atcggcgtgg gcgaagtgct ggaccggggc gacgaagtgc ccagcctgtt catgaccaac    720
gtgtggaccc cccccaaccc caacaccgtg taccactgca cgccgtgta caacaacgag     780
ttctactacg tgctgtgcgc cgtgagcacc gtgggcgacc ccatcctgaa cagcacctac    840
tggagcggca gcctgatgat gacccggctg gccgtgaagc taagagcaa cggcggaggc    900
tacaaccagc accagctggc cctgcggagc atcgagaagg gccggtacga caaagtgatg    960
ccctacggcc ccagcggcat caagcagggc gacaccctgt acttccccgc cgtgggcttc   1020
ctggtgcgga ccgagttcaa gtacaacgac agcaactgcc ccatcaccaa gtgccagtac    1080
agcaagcccg agaactgccg gctgagcatg ggcatccggc caacagcca ctacatcctg   1140
cggagcggcc tgctgaagta caacctgagc gacggcgaga cccccaaagt ggtgttcatc    1200
```

-continued

```
gagatcagcg accagagact gagcatcggc agccccagca agatctacga cagcctgggc    1260
cagcccgtgt tctaccaggc cagcttcagc tgggacacca tgatcaagtt cggcgacgtg    1320
ctgaccgtga acccctggt  ggtgaactgg cggaacaata ccgtgatcag cagacccggc    1380
cagagccagt gccccggtt  caacacctgc cccgagatct gctgggaggg cgtgtacaac    1440
gacgccttcc tgatcgaccg gatcaactgg atcagcgccg gagtgttcct ggatagcaac    1500
cagaccgccg agaatcccgt gttcaccgtg tttaaggaca acgagatcct gtacagagcc    1560
cagctggcca gcgaggacac caacgcccag aaaaccatca ccaactgctt cctgctgaag    1620
aataagatct ggtgcatcag cctggtggag atctacgata ccggcgacaa cgtgatcagg    1680
cccaagctgt tcgccgtgaa gatccccgag cagtgctacc cctacgacgt gcccgactac    1740
gcctga                                                              1746
```